(12) United States Patent
De Haan et al.

(10) Patent No.: US 11,089,412 B2
(45) Date of Patent: Aug. 10, 2021

(54) HEARING DEVICE COMPRISING A SENSOR CONFIGURATION DETECTOR

(71) Applicant: Oticon A/S, Smørum (DK)

(72) Inventors: Jan M. De Haan, Smørum (DK); Angela Josupeit, Smørum (DK); Sara Klimt-Møllenbach, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 16/811,543

(22) Filed: Mar. 6, 2020

(65) Prior Publication Data

US 2020/0288253 A1   Sep. 10, 2020

(30) Foreign Application Priority Data

Mar. 7, 2019   (EP) .................................... 19161283

(51) Int. Cl.
*H04R 25/00*   (2006.01)

(52) U.S. Cl.
CPC ......... *H04R 25/556* (2013.01); *H04R 25/558* (2013.01); *H04R 25/606* (2013.01); *H04R 25/70* (2013.01); *H04R 2225/021* (2013.01); *H04R 2225/025* (2013.01)

(58) Field of Classification Search
CPC .. H04R 25/556; H04R 25/558; H04R 25/606; H04R 25/70; H04R 2225/021; H04R 2225/025
USPC ........................................................ 381/312
See application file for complete search history.

(56) References Cited

U.S. PATENT DOCUMENTS

| 2003/0031336 | A1* | 2/2003 | Harrison | H04R 25/48 381/330 |
| 2010/0101892 | A1 | 4/2010 | Elders et al. | |
| 2010/0124346 | A1* | 5/2010 | Higgins | H04R 25/55 381/312 |
| 2012/0109297 | A1* | 5/2012 | Van den Heuvel | H04R 25/606 623/10 |
| 2016/0360328 | A1 | 12/2016 | Schmidt et al. | |

(Continued)

FOREIGN PATENT DOCUMENTS

| EP | 2 200 347 A2 | 6/2010 |
| EP | 2 843 971 A1 | 3/2015 |

(Continued)

*Primary Examiner* — Sean H Nguyen
(74) *Attorney, Agent, or Firm* — Birch, Stewart, Kolasch & Birch, LLP

(57) ABSTRACT

A hearing device, e.g. a hearing aid, comprises first and second hearing device parts having separate first and second housings and being electrically connectable by a connecting element. The second hearing device part is available in a multitude of variants. The connecting element comprises an electric cable comprising a multitude of electric conductors, and a first electric connector comprising a multitude of first electric termination elements. The second hearing device part comprises a loudspeaker, and/or a number of sensors each providing an electric sensor signal representative of a current property of the environment of the hearing device and/or a current state of the user wearing the hearing device. The first hearing device part comprises a configuration extractor electrically connected to said second hearing device part via said connecting element and adapted to identify a current configuration of sensors in said second hearing device part.

27 Claims, 11 Drawing Sheets

(56) References Cited

U.S. PATENT DOCUMENTS

2017/0013374 A1   1/2017  Larsen et al.
2017/0180882 A1   6/2017  Lunner et al.
2017/0359662 A1  12/2017  Higgins et al.

FOREIGN PATENT DOCUMENTS

EP         3 313 092 A1   4/2018
WO   WO 2009/065742 A1   5/2009

\* cited by examiner

| CONF#1 | CONF#2 | CONF#3 | CONF#4 | CONF#5 | CONF#6 |
|---|---|---|---|---|---|
| SPK | SPK | SPK | SPK | SPK | SPK |
| Nothing | MIC#1 | MIC#1 | MIC#1 | SEN#1 | SEN#1 |
| Nothing | Nothing | MIC#2 | SEN#1 | Nothing | SEN#2 |
| bfctr=0 spctr=0 | bfctr=1 spctr=0 | bfctr=2 spctr=0 | bfctr=1 spctr=1 | bfctr=0 spctr=1 | bfctr=0 spctr=2 |

FIG. 6

HEARING DEVICE COMPRISING A SENSOR CONFIGURATION DETECTOR

SUMMARY

The present application deals with hearing devices, e.g. hearing aids, in particular with a hearing device comprising first and second electrically connectable parts, at least one of the parts being available in a multitude of variants.

A Hearing Device

In an aspect of the present application, a hearing device, e.g. a hearing aid, adapted for being located at or in an ear of a user is provided. The hearing device comprises
- first and second electrically connectable hearing device parts having separate first and second housings, at least the second hearing device part being available in a multitude of variants, each variant providing different functionality to the hearing device,
- a connecting element configured to electrically connect the first hearing device part and the second hearing device part, the connecting element comprising
  - an electric cable comprising a multitude of electric conductors,
  - a first electric connector comprising a multitude of first electric termination elements electrically connected to said multitude of electric conductors, the first electric connector being configured to be mechanically and electrically joined with a matching second electric connector.

The first or second hearing device part comprises said second electric connector. The second electric connector comprises a multitude of second electric termination elements electrically connected to electric components of the first or second hearing device part, respectively, and configured to electrically connect conductors of the cable with said electric components of the first and second hearing device parts when the first and second electric connectors are joined.

The second hearing device part comprises
- a loudspeaker, and/or
- a number of sensors for sensing
  - a current property of the environment of the hearing device; and/or
  - a current state of the user wearing the hearing device.

Each of said number of sensors provides an electric sensor signal representative of a property of the environment or a state of the user, wherein said loudspeaker and/or said number of sensors are electrically connected to said first hearing device part via said connecting element. The first hearing device part or a programming device electrically connected to the first hearing device part comprises a configuration extractor electrically connected to said second hearing device part via said connecting element and adapted to identify a current configuration of sensors in said second hearing device part.

Thereby a more flexible hearing device may be provided.

The first and second electric connectors may be of a plug and socket type, respectively (or a male-female type, or a mixture thereof). The first and/or second electric termination elements may comprise one or more pins, e.g. a multitude of pins. The first and/or second electric termination elements may comprise flat conductors located on a slab carrier, e.g. a number of separate electric termination elements on each side of a slab carrier, e.g. three or four electric termination elements on each side thereby implementing six or eight separate electric termination elements. The number of first and/or second electric termination elements may be equal to the number of conductors of the cable.

The configuration extractor may be adapted to identify a current configuration of sensors in said second hearing device part among a limited number of known configurations of sensors. A current property of the environment of the hearing device may comprise an acoustic vibration (sound). A sensor of a current property of the environment of the hearing device may be a sound sensor.

The number of sensors may comprise a microphone. All of the sensors may be microphones. The number of sensors may comprise an acousto-electric sensor, e.g. a piezoelectric sensor.

The number of sensors may comprise a light-sensitive sensor. The number of sensors may comprise a PPG-sensor (PPG=photoplethysmogram).

The number of sensors may comprise a brainwave sensor. A brainwave sensor may e.g. comprise an EEG-sensor, an EOG-sensor, or an MEG-sensor. The number of sensors may comprise a biometric sensor, e.g. for identifying the person wearing the hearing device. The number of sensors may comprise a movement sensor, e.g. an accelerometer and/or a gyroscope.

At least one of the electric conductors of the electric cable may, at least in a specific mode of operation of the hearing device, be allocated for use by one of the number of sensors The second hearing device part may be configured to host a maximum number of sensors. The second hearing device part may be configured to host a maximum number $N_S$ of sensors, e.g. one or two, or three, or four, or more. The number of electric sensors (located in the second hearing device part at a given time) may be smaller than or equal to the maximum number $N_s$ of sensors for a given type of second hearing device part.

Each of the number of sensors may be allocated a different one of the number of electric termination elements and associated electric conductors of the cable to transfer a respective electric sensor signal to the first hearing device part. The number of electric termination elements and associated conductors of the electric cable of the connecting element may be adapted to the number of sensors. Each electric termination element may be connected to an electric conductor. Each electric conductor may be connected to an electric termination element. The number of electric termination element may be equal to the number of electric conductors.

At least one of the electric termination elements and associated electric conductors of the cable are allocated to a supply voltage, or a voltage derived therefrom. Two of the electric termination elements and electric conductors of the cable may be allocated to a supply voltage (e.g. +VDD, −VDD, or +VDD, GND). Three of the electric termination elements and electric conductors of the cable may be allocated to a supply voltage (e.g. +VDD, −VDD, GND). In an embodiment, two electric termination elements and two electric conductors are allocated to a positive and a negative supply voltage and one electric termination element and one electric conductor per sensor (be it a microphone or other sensors). Two electric termination elements and two electric conductors may further be allocated to a loudspeaker. In an embodiment of a second hearing device part comprising a loudspeaker and a number of sensors, four electric termination elements and four electric conductors are allocated to supply voltages and loudspeaker terminals, so a total number of electric termination elements and electric conductors $N_{TC}$ for a second hearing device part comprising $N_S$ sensors may be expressed as $N_{TC}=4+N_S$. The cable may comprise one or more conductors for other purposes (than sensing properties or transducing sound), e.g. for acting as an antenna for a wireless interface, e.g. Bluetooth or similar technology working in the MHz or GHz frequency range.

Each of said number of electric sensors provides an electric sensor signal having predetermined characteristics. The predetermined characteristics may include a voltage range (within which the electric sensor signal takes on values), an inherent noise level, a typical (e.g. average) frequency spectrum (e.g. predefined frequency range(s), where content is expected), an average signal level, a level modulation, etc. The inherent noise level (e.g. due to shot noise and/or thermally induced noise) is taken to mean the output of the sensor (i.e. the electric sensor signal), when no stimulation by the property (e.g. light or sound) it senses, is provided. If, for example, the sensor is a microphone, no acoustic input signal would result in the electric sensor signal reflecting the inherent microphone noise. A given type of second hearing device part may be configured to receive a number of sensors, each being of predetermined kind (e.g. a PPG-sensor, a temperature sensor, and an EEG-sensor) having predetermined characteristics. The predetermined characteristics of the predetermined kinds of sensors may be known to the hearing device. The predetermined characteristics may e.g. be measured in advance of use of the hearing device, and e.g. stored in a memory of the hearing device, or otherwise be accessible to the hearing device or to a fitting system connectable to the hearing device. A given sensor signal may e.g. be characterized by its sampling rate, or by a degree of periodicity, e.g. by periodic 'events' (e.g. peaks) occurring in the signal (e.g. from a heart beat detector or a movement detector). In case the sensor has a digital output, a kind of sensor may e.g. be communicated by the sensor itself (a 'sensor signature') via its allocated conductor (or a conductor dedicated to data) to the configuration extractor and identified there, e.g. in a decoder.

An electric termination element and associated electric conductor of the cable, which is allocated to a specific one of the number of sensors, may be supplied with a predefined signal, when said specific sensor is absent from said second hearing device part. The predefined signal may e.g. be a signal with a known (easily detectable) waveform, e.g. a sinus tone. Preferably, the predefined signal may be a constant voltage, e.g. a supply voltage (e.g. +VDD, −VDD) or ground. The configuration extractor may be specifically adapted to detect the predefined signal (e.g. comprising a matched filter, or a detector of a constant voltage).

The configuration extractor may e.g. be configured to analyse the sensor signal by applying a successively lower sampling rate to the signal (from high to low) to thereby be able to identify fast varying signals (first). Thereby different characteristics of the sensor signals may be determined and a kind of sensor identified. The configuration extractor may e.g. be configured to identify the presence of a microphone by making a correlation measurement with one or more signals from other microphones (e.g. microphones of the first hearing device part, e.g. a BTE-part) that can be assumed to receive sound from the same sound field as the sensor (microphone) located in the second hearing device part (e.g. an ITE-part).

At least one of the number of sensors may have a digital output and is adapted to communicate an identifier of said sensor to the first hearing device part via its allocated conductor or a conductor dedicated to data. The configuration extractor may be adapted to decode said identifier. The identifier may be automatically transmitted when the sensor is powered up. The identifier may be a (possibly) coded information indicating the kind of sensor, and possibly its main characteristics.

At least one of the number of sensors may have an analogue output. The configuration extractor may be adapted to identify the sensor based on its intrinsic noise signal and/or on an output signal from the sensor reflecting its normal function. The use of sensors with analogue inputs may be advantageous for low latency applications, e.g. transient detection, active noise cancellation, etc.

At least one of the number of sensors may have an analogue as well as a digital output. Thereby an initial identification (signature) of the sensor may be issued as a digital output, while the functional sensor output may be analogue. The use of a digital output or an analogue (functional) output from the sensor may be configurable (selectable).

The second hearing device part may be adapted to be located at least partially in an ear canal of the user.

The number of sensors may comprise a microphone intended to face the ear drum when the second hearing device part is located at or in an ear of the user. The configuration extractor may be adapted to detect the user's heartbeat in the output signal from the microphone, and to thereby identify the sensor as an inward facing microphone.

The number of sensors may comprise a microphone. The hearing device may be configured to play a test sound signal, and the configuration extractor may be adapted to detect the test sound signal in the feedback signal received by said microphone, and to thereby identify the sensor as a microphone.

The hearing device may be configured to identify each of the number of sensors individually to thereby identify the current configuration of sensors in the second hearing device part.

The configuration extractor may be adapted to compare an electric sensor signal from a particular sensor among the number of sensors before and after being located at or in an ear of a user, and based thereon, to identify the particular sensor. Examples of sensors that may exhibit significantly different signals before (e.g. while lying on a flat surface, e.g. a table) and after being mounted at or in the ear of the user are a) brainwave or other biometric sensors, such as EEG, EOG, MEG-sensors, and b) light sensitive sensors, such as photo diodes.

The hearing device may be configured to control the use of the number of sensors in the hearing device. The hearing device may be configured to control processing of microphone signals (e.g. located in the first and optionally second hearing device parts) based on the configuration identified current configuration of sensors in the second hearing device part. The processing may include control of beamforming (which microphones are fed to the beamformer filter and included in the determination of the beamformed signal) or other signal processing algorithms, e.g. based on sensors located in the second hearing device part.

The hearing device may be configured to control the use of the number of sensors in the hearing device in dependence of a mode of operation. A given sensor in the second hearing device part may e.g. only be used in one or more particular modes of operation of the hearing device. A microphone located in the second hearing device part may e.g. only be used in one or more specific modes of operation, e.g. a 'handsfree telephone' mode. None, or a subset of the number of sensors may be active in a 'sleep' or 'low-power' mode.

Thereby power can be saved in the hearing device. One or more of the sensors may be activated in a 'high cognitive load' mode of operation.

The hearing device may be constituted by or comprise a hearing aid, a headset, an earphone, an ear protection device or a combination thereof.

The hearing device may comprise a user communication interface, e.g. a wireless user communication interface, allowing a user to influence functionality of the hearing device via a user interface. The user communication interface may be a wireless communication interface, e.g. based on Bluetooth or Bluetooth Low Energy, or similar (standardized or proprietary) technology.

In an embodiment, the hearing device is adapted to provide a frequency dependent gain and/or a level dependent compression and/or a transposition (with or without frequency compression) of one or more frequency ranges to one or more other frequency ranges, e.g. to compensate for a hearing impairment of a user. In an embodiment, the hearing device comprises a signal processor for enhancing the input signals and providing a processed output signal.

In an embodiment, the hearing device comprises an output unit for providing a stimulus perceived by the user as an acoustic signal based on a processed electric signal. In an embodiment, the output unit comprises a number of electrodes of a cochlear implant (for a CI type hearing device) or a vibrator of a bone conducting hearing device. In an embodiment, the output unit comprises an output transducer. In an embodiment, the output transducer comprises a receiver (loudspeaker) for providing the stimulus as an acoustic signal to the user (e.g. in an acoustic (air conduction based) hearing device). In an embodiment, the output transducer comprises a vibrator for providing the stimulus as mechanical vibration of a skull bone to the user (e.g. in a bone-attached or bone-anchored hearing device).

In an embodiment, the hearing device comprises an input unit for providing an electric input signal representing sound. In an embodiment, the input unit comprises an input transducer, e.g. a microphone, for converting an input sound to an electric input signal. In an embodiment, the input unit comprises a wireless receiver for receiving a wireless signal comprising sound and for providing an electric input signal representing said sound.

In an embodiment, the hearing device comprises a directional microphone system adapted to spatially filter sounds from the environment, and thereby enhance a target acoustic source among a multitude of acoustic sources in the local environment of the user wearing the hearing device. In an embodiment, the directional system is adapted to detect (such as adaptively detect) from which direction a particular part of the microphone signal originates. This can be achieved in various different ways as e.g. described in the prior art. In hearing devices, a microphone array beamformer is often used for spatially attenuating background noise sources. Many beamformer variants can be found in literature. The minimum variance distortionless response (MVDR) beamformer is widely used in microphone array signal processing. Ideally the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form.

In an embodiment, the hearing device comprises an antenna and transceiver circuitry (e.g. a wireless receiver) for wirelessly receiving a direct electric input signal from another device, e.g. from an entertainment device (e.g. a TV-set), a communication device, a wireless microphone, or another hearing device. In an embodiment, the direct electric input signal represents or comprises an audio signal and/or a control signal and/or an information signal. In an embodiment, the hearing device comprises demodulation circuitry for demodulating the received direct electric input to provide the direct electric input signal representing an audio signal and/or a control signal e.g. for setting an operational parameter (e.g. volume) and/or a processing parameter of the hearing device. In general, a wireless link established by antenna and transceiver circuitry of the hearing device can be of any type. In an embodiment, the wireless link is established between two devices, e.g. between an entertainment device (e.g. a TV) and the hearing device, or between two hearing devices, e.g. via a third, intermediate device (e.g. a processing device, such as a remote control device, a smartphone, etc.). In an embodiment, the wireless link is used under power constraints, e.g. in that the hearing device is or comprises a portable (typically battery driven) device. In an embodiment, the wireless link is a link based on near-field communication, e.g. an inductive link based on an inductive coupling between antenna coils of transmitter and receiver parts. In another embodiment, the wireless link is based on far-field, electromagnetic radiation.

Preferably, frequencies used to establish a communication link between the hearing device and the other device is in an ISM range (ISM=Industrial, Scientific and Medical, such standardized ranges being e.g. defined by the International Telecommunication Union, ITU). The wireless link may be based on a standardized or proprietary technology. The wireless link may be based on Bluetooth technology (e.g. Bluetooth Low-Energy technology).

In an embodiment, the hearing device has a maximum outer dimension of the order of 0.08 m (e.g. a headset). In an embodiment, the hearing device has a maximum outer dimension of the order of 0.04 m (e.g. a hearing instrument).

In an embodiment, the hearing device is a portable (i.e. configured to be wearable) device, e.g. a device comprising a local energy source, e.g. a battery, e.g. a rechargeable battery. The hearing device is e.g. a low weight, easily wearable, device, e.g. having a total weight less than 100 g.

The hearing device may comprise a forward or signal path between an input unit (e.g. an input transducer, such as a microphone or a microphone system and/or direct electric input (e.g. a wireless receiver)) and an output unit, e.g. an output transducer. In an embodiment, the signal processor is located in the forward path. In an embodiment, the signal processor is adapted to provide a frequency dependent gain according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing devices comprise an analogue-to-digital (AD) converter to digitize an analogue input (e.g. from an input transducer, such as a microphone) with a predefined sampling rate, e.g. 20 kHz. In an embodiment, the hearing devices comprise a digital-to-analogue (DA) converter to convert a digital signal to an analogue output signal, e.g. for being presented to a user via an output transducer.

In an embodiment, the hearing device, e.g. the microphone unit, and or the transceiver unit comprise(s) a TF-conversion unit for providing a time-frequency representation of an input signal.

In an embodiment, the hearing device comprises a number of detectors or sensors configured to provide status signals relating to a current physical environment of the hearing device (e.g. the current acoustic environment), and/or to a current state of the user wearing the hearing device, and/or to a current state or mode of operation of the hearing device. Alternatively or additionally, one or more detectors may form part of an external device in communication (e.g. wirelessly) with the hearing device. An external device may e.g. comprise another hearing device, a remote control, and audio delivery device, a telephone (e.g. a smartphone), an external sensor, etc.

In an embodiment, one or more of the number of detectors operate(s) on the full band signal (time domain). In an embodiment, one or more of the number of detectors operate(s) on band split signals ((time-) frequency domain), e.g. in a limited number of frequency bands.

In an embodiment, the number of detectors comprises a level detector for estimating a current level of a signal of the forward path. In an embodiment, the predefined criterion comprises whether the current level of a signal of the forward path is above or below a given (L-)threshold value. In an embodiment, the level detector operates on the full band signal (time domain). In an embodiment, the level detector operates on band split signals ((time-) frequency domain).

In a particular embodiment, the hearing device comprises a voice detector (VD) for estimating whether or not (or with what probability) an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the hearing device comprises an own voice detector for estimating whether or not (or with what probability) a given input sound (e.g. a voice, e.g. speech) originates from the voice of the user of the system. In an embodiment, a microphone system of the hearing device is adapted to be able to differentiate between a user's own voice and another person's voice and possibly from NON-voice sounds.

In an embodiment, the number of detectors comprises a movement detector, e.g. an acceleration sensor. In an embodiment, the movement detector is configured to detect movement of the user's facial muscles and/or bones, e.g. due to speech or chewing (e.g. jaw movement) and to provide a detector signal indicative thereof.

In an embodiment, the hearing device comprises a classification unit configured to classify the current situation based on input signals from (at least some of) the detectors, and possibly other inputs as well. In the present context 'a current situation' is taken to be defined by one or more of a) the physical environment (e.g. including the current electromagnetic environment, e.g. the occurrence of electromagnetic signals (e.g. comprising audio and/or control signals) intended or not intended for reception by the hearing device, or other properties of the current environment than acoustic, e.g. light conditions, temperature, humidity, geographical location, height above sea level, etc.);

b) the current acoustic situation (input level, feedback, etc.), and c) the current mode or state of the user (movement, temperature, cognitive load, etc.);

d) the current mode or state of the hearing device (program selected, time elapsed since last user interaction, etc.) and/or of another device in communication with the hearing device.

Sensors related to a current mode or state of the user may e.g. be located in the ITE-part.

A sensor for inclusion in the hearing device may e.g. be or comprise a temperature sensor, e.g. adapted to log temperature over time to be able to determine a rate of change of temperature. The temperature sensor may be configured for measuring the body or skin temperature of the wearer of the hearing device (e.g. at those parts of the hearing device, e.g. the ITE-part, that have skin contact while the hearing device is being worn). A temperature sensor may e.g. be used to detect whether or not the hearing device is being worn. This may e.g. be concluded (indicated), if the measured temperature has decreased more than a predefined value, e.g. more than $1°$ K, or more than $2°$ K, or more than $5°$ K, within a predefined time span, e.g. within the last 5 minutes, or within the last hour. The hearing device is configured to receive a control input from an external temperature sensor, e.g. providing a current temperature of the environment. The hearing device may e.g. be configured to transmit a current temperature (and/or a rate of change of temperature) to a remote control device, e.g. to an APP or a smartphone.

A sensor for inclusion in the hearing device may e.g. be or comprise a light intensity sensor (e.g. located at a place on the hearing device's shell that is covered with or touches the user's skin while the hearing device is worn and (probably) less covered when the hearing device is not worn). The light sensor may e.g. be or comprise a photodiode (e.g. for detecting infrared light), e.g. be a photoplethysmogram (PPG) sensor, e.g. a pulse oximeter, e.g. for monitoring the cardiac circle of the wearer of the hearing device. The hearing device may e.g. be configured to transmit a current estimate of the heart rate of the user (e.g. provided by a PPG-sensor signal) to a remote control device, e.g. to an APP or a smartphone.

A sensor for inclusion in the hearing device may e.g. be or comprise a body sound detector (e.g. the sound of the human heart beat while the hearing device is worn). This parameter can contribute to indicating a current state of the user (asleep vs. exercising, e.g. or worn, not worn), e.g. by comparison with stored reference values.

A sensor for inclusion in the hearing device may e.g. be or comprise an electrical conductivity detector (e.g. the conductivity between contact points on the housing of the hearing device, e.g. of human skin while the hearing device is worn to thereby contribute to decide whether or not the hearing device is currently being worn, e.g. by comparison with stored reference values).

A sensor for inclusion in the hearing device may e.g. be or comprise a movement detector, e.g. an accelerometer for detecting a linear movement of the hearing device, and/or a detector of a change of angular momentum on the hearing device (e.g. gyroscope). These parameters can contribute to indicating a current state of the user (asleep vs. exercising, etc. or a state or environmental condition of the hearing device, worn or not worn). MEMS acceleration sensors are e.g. available from Bosch Sensortec or Analog Devices.

A sensor for inclusion in the hearing device may e.g. be or comprise a detector of body signals, e.g. brain waves to indicate present state of mind or cognitive load (e.g. using EEG-electrodes or -sensors (EEG=Electro-encephalography), e.g. located on a shell or housing part (e.g. the ITE-part) of the hearing device, cf. e.g. EP2200347A2, or MEG-sensors (MEG=Magneto-encephalography)), or eye gaze using electrooculography (see e.g. US20170180882A1).

In an embodiment, the hearing device further comprises other relevant functionality for the application in question, e.g. compression, noise reduction, feedback control, etc.

In an embodiment, the hearing device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof. In an embodiment, the hearing system comprises a speakerphone (comprising a number of input transducers and a number of output transducers, e.g. for use in an audio conference situation), e.g. comprising a beamformer filtering unit, e.g. providing multiple beamforming capabilities.

Use

In an aspect, use of a hearing device as described above, in the 'detailed description of embodiments' and in the claims, is moreover provided. In an embodiment, use is provided in a system comprising audio distribution. In an embodiment, use is provided in a system comprising one or more hearing aids (e.g. hearing instruments), headsets, ear phones, active ear protection systems, etc., e.g. in handsfree telephone systems, teleconferencing systems (e.g. including a speakerphone), public address systems, karaoke systems, classroom amplification systems, etc.

A Data Processing System

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing System

In a further aspect, a hearing system comprising a hearing device as described above, in the 'detailed description of embodiments', and in the claims, AND an auxiliary device is moreover provided. The auxiliary device may be or comprise a programming device for programming the hearing device. The programming device may run a fitting software for configuring a hearing device to a particular user's needs.

The hearing system may comprise a hearing device, e.g. a hearing aid, and a programming device for configuring the hearing device.

The hearing device comprises
  first and second electrically connectable hearing device parts having separate first and second housings, at least the second hearing device part being available in a multitude of variants, each variant providing different functionality to the hearing device,
  a connecting element configured to electrically connect the first hearing device part and the second hearing device part, the connecting element comprising
    an electric cable comprising a multitude of electric conductors,
    a first electric connector comprising a multitude of first electric termination elements electrically connected to said multitude of electric conductors, the first electric connector being configured to be mechanically and electrically joined with a matching second electric connector;
  the first or second hearing device part comprising
    said second electric connector, said second electric connector comprising a multitude of second electric termination elements electrically connected to electric components of the first or second hearing device part, respectively, and configured to electrically connect conductors of the cable with said electric components of the first and second hearing device parts when the first and second electric connectors are joined,
  the second hearing device part comprising
    a loudspeaker, and/or
    a number of sensors for sensing
      a current property of the environment of the hearing device; and/or
      a current state of the user wearing the hearing device,
    each of said number of sensors providing an electric sensor signal representative of a property of the environment or a state of the user, wherein said loudspeaker and/or said number of sensors are electrically connected to said first hearing device part via said connecting element,
  the first hearing device part comprising a programming interface to the programming device.

The programming device comprises a configuration extractor electrically connected to said second hearing device part via said programming interface and said connecting element and adapted to identify a current configuration of sensors in said second hearing device part.

The programming device may be configured to control the use of the sensors in the hearing device. The programming device may be configured to run a fitting software for the hearing device.

The hearing system may be configured to identify each of the number of sensors individually to thereby identify the current configuration of sensors in said second hearing device part.

In an embodiment, the hearing system is adapted to establish a communication link between the hearing device and the auxiliary device to provide that information (e.g. control and status signals, possibly audio signals) can be exchanged or forwarded from one to the other.

In an embodiment, the hearing system comprises an auxiliary device, e.g. a remote control, a smartphone, or other portable or wearable electronic device, such as a smartwatch, etc.

In an embodiment, the auxiliary device is or comprises a remote control for controlling functionality and operation of the hearing device(s). In an embodiment, the function of a remote control is implemented in a smartphone, the smartphone possibly running an APP allowing to control the functionality of the audio processing device via the smartphone (the hearing device(s) comprising an appropriate wireless interface to the smartphone, e.g. based on Bluetooth or some other standardized or proprietary scheme).

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing device.

In an embodiment, the auxiliary device is or comprises another hearing device. In an embodiment, the hearing system comprises two hearing devices adapted to implement a binaural hearing system, e.g. a binaural hearing aid system.

An APP

In a further aspect, a non-transitory application, termed an APP, is furthermore provided by the present disclosure. The APP comprises executable instructions configured to be executed on an auxiliary device to implement a user interface for a hearing device or a hearing system described above in the 'detailed description of embodiments', and in the claims. In an embodiment, the APP is configured to run on cellular phone, e.g. a smartphone, or on another portable device allowing communication with said hearing device or said hearing system.

Definitions

In the present context, a 'hearing device' refers to a device, such as a hearing aid, e.g. a hearing instrument, or an active ear-protection device, or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing device may comprise a single unit or several units communicating electronically with each other. The loudspeaker may be arranged in a housing together with other components of the hearing device, or may be an external unit in itself (possibly in combination with a flexible guiding element, e.g. a dome-like element).

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing devices, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output unit may comprise an output transducer, such as e.g. a loudspeaker for providing an air-borne acoustic signal or a vibrator for providing a structure-borne or liquid-borne acoustic signal. In some hearing devices, the output unit may comprise one or more output electrodes for providing electric signals (e.g. a multi-electrode array for electrically stimulating the cochlear nerve). In an embodiment, the hearing device comprises a speakerphone (comprising a number of input transducers and a number of output transducers, e.g. for use in an audio conference situation).

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing device, e.g. a hearing aid, may be adapted to a particular user's needs, e.g. a hearing impairment. A configurable signal processing circuit of the hearing device may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing device via an interface to a programming device (fitting system) and used by a processing algorithm executed by the configurable signal processing circuit of the hearing device.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. smartphones), or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person. Hearing devices or hearing systems may e.g. form part of or interact with public-address systems, active ear protection systems, handsfree telephone systems, car audio systems, entertainment (e.g. karaoke) systems, teleconferencing systems, classroom amplification systems, etc.

Embodiments of the disclosure may e.g. be useful in applications such as portable hearing devices (wearables'), comprising a main part and an accessory part that comes in a multitude of variants, e.g. hearing aids comprising at least two interconnectable parts, e.g. receiver in the ear style hearing aids.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 6 shows a table listing possible combinations of sensors in the form of microphones and other sensors for an exemplary ITE part of a hearing device according to the present disclosure, and corresponding configuration control indicators.

The figures are schematic and simplified for clarity, and they just show details which are essential to the understanding of the disclosure, while other details are left out. Throughout, the same reference signs are used for identical or corresponding parts.

Figure 1A:
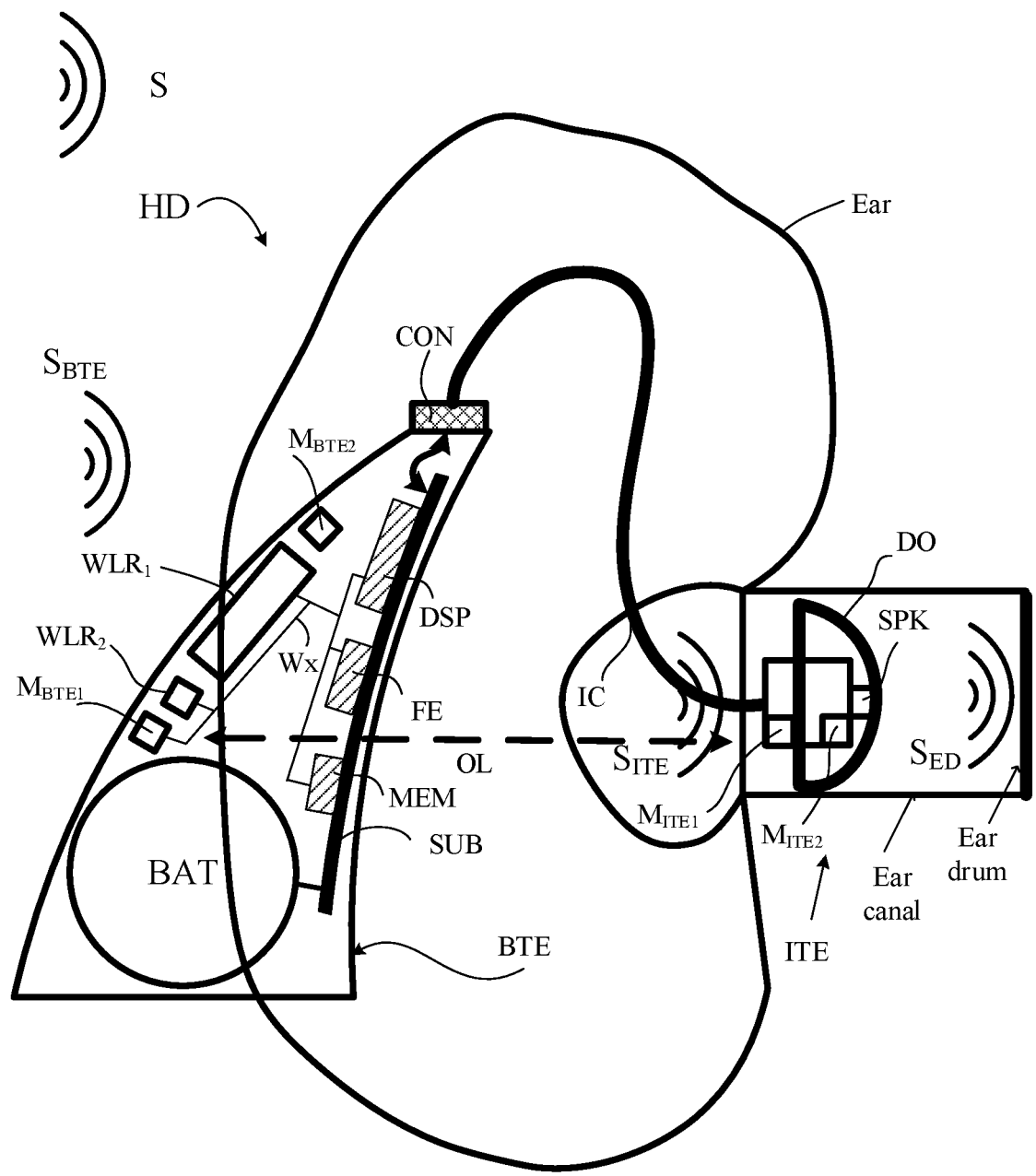
FIG. 1A shows a first embodiment of a hearing device comprising a BTE-part and an ITE-part according to the present disclosure.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of portable hearing devices, e.g. hearing aids, e.g. to hearing aids comprising two separate parts electrically connected by a connecting element, where one of the parts is available in a multitude of variants. The disclosure may e.g. relate to a hearing aid comprising an input transducer, e.g. a microphone, located in or at an ear canal of a user wearing the hearing aid. In some hearing aids, an extra microphone is added to a conventional state of the art hearing aid comprising a behind the ear (BTE) part wherein one or two (or more) input transducers (e.g. microphones, termed BTE-microphones) are located. The extra (e.g. third) microphone (in the following also referred to as the 'in the ear (ITE) microphone') is placed at or in the ear, e.g. forming part of an ITE-part located at or in the ear canal. In some hearing aid styles, sometimes termed 'receiver in the ear' (RITE) type hearing aids, a loudspeaker of the hearing aid (the loudspeaker being often also termed the 'receiver' in the field of hearing aids) is also located at or in the ear canal, e.g.

in the same ITE-part (e.g. termed the 'receiver unit') as the ITE-microphone. The BTE-part and the ITE-part are electrically connected, e.g. via an electric cable comprising a multitude of electric conductors (e.g. electrically conducting, e.g. metallic, wires). The electric cable is electrically terminated in the respective BTE- and ITE-parts allowing electric connection of the multitude of electric conductors to respective parts (e.g. electronic parts) of the BTE- and ITE-parts. At least one of the electric conductors of the electric cable is (at least partially, e.g. in a specific mode of operation) allocated for use by the ITE-microphone. The electric cable may comprise an electric connector (e.g. at one end or at both ends) to facilitate easy exchange of the ITE-part with another ITE-part of the same a different configuration. The electric connector may comprise a first connector part, which when mechanically joined with a matching second connector part (e.g. integrated with a housing of the BTE-part and/or the ITE part) electrically connects the cable with the part or device wherein the second connector part is located. The first and second connector parts may be of a plug and socket type (or a male-female type, or a mixture thereof). The first and/or second connector parts may comprise a number of pins, e.g. a multitude of pins and corresponding holes in mating (second and/or first) connector for receiving the pins (or other electric terminal elements, e.g. flat conductive strips on a slab carrier and corresponding strips on a mating receiving connector).

For some features and use cases, it might be of importance to know whether the currently connected receiver unit (ITE-part) contains a microphone (or other sensor) or not, and if it does, whether or not the microphone (or other sensor) is functioning (not dead or otherwise malfunctioning). As an example, this knowledge might be interesting within the fitting procedure. During the fitting procedure a hearing aid is adapted (fitted) by a hearing care professional to the user's particular needs, e.g. regarding frequency shaping of the acoustic input signal (e.g. amplification) to compensate for the user's hearing impairment. The automatic detection of the currently connected receiver (loudspeaker) type eases the Hearing Care Professional's work, and it facilitates the selection of specific fitting settings and software configuration that could vary based on the receiver type. The (automatic) detection of a type of loudspeaker (receiver) in a given loudspeaker unit has been dealt with in numerous documents, e.g. in WO2009065742A1. Various ways of identifying a type of loudspeaker (or of particular properties of the loudspeaker, e.g. its frequency dependent impedance or the like) have been proposed, e.g. by reading an identity from a memory, or by identifying a particular component, located in the (exchangeable) loudspeaker unit.

The knowledge about the presence and status of the ITE-microphone (or other sensor) may also be of particular interest for specific signal processing features. In the case of a not-available or dead ITE-microphone, specific signal paths involving the ITE-microphone may for example be switched off, so that only the BTE microphone(s) (and the corresponding directivity features) are utilized.

In the present disclosure, a solution for detecting the ITE-microphone (or other sensors) and its status based on the response behaviour of the connection pins between a BTE-part and an ITE-part (e.g. a receiver unit) of a (portable/wearable) hearing device is proposed.

The electric cable and connector for connecting a BTE-part to an ITE-part comprising (only) a loudspeaker may e.g. be configured to connect to three electric conductors (e.g. using three connection pins). In case the ITE-part comprises more functional components, e.g. an extra microphone, the electric cable and connector is preferably configured to comprise and connect to more than three electric conductors (e.g. to five or six (or more conductors), e.g. using 5 or 6 (or more) connection pins (or other electric termination elements) in the connector). ITE-parts without an extra microphone should still be connectable to BTE-parts (with the same connecting element), so the cable and connector may have the same number of conductors and connection pins (as when an extra microphone is present in the ITE-part), but some of these may not have any function (or have a different function).

To differentiate between the ITE-parts with and without (the extra) microphone, it is suggested to monitor the response behaviour at the electric connections to the ITE-part. In case of a connected ITE-part comprising a microphone, the corresponding connection response would result in some microphone noise (if no environment sound is present). In case of a receiver unit without a microphone, the corresponding connections could be connected to a known signal, e.g. a supply voltage, and thus not result in any microphone noise.

The status of a connected ITE-microphone (or another sensor), i.e., whether it is functioning or dead, may be monitored. A dead-microphone (or other sensor)-detection method based on a long-term signal level average may be applied. A predetermined (reference) long-term level estimate for the broadband microphone signal may be stored in the hearing device. During use of the hearing device the long-term level estimate is monitored and compared to the reference long term level estimate. If a deviation of more than a predefined amount is determined, the microphone is not relied on, e.g. its signal is not used for generating a directional signal (or for other uses it might be configured to form part of). Instead of being compared to a stored reference long term level estimate of the ITE-microphone, the long term level estimate during use may be compared to a long term level estimate of one or more other microphones of the hearing device, e.g. in the BTE-part.

FIGS. 1A, 2A, 3A, and 4A, each shows an exemplary hearing device according to the present disclosure. The hearing device (HD), e.g. a hearing aid, is of a particular style (sometimes termed receiver-in-the ear, or RITE, style) comprising a BTE-part (BTE) adapted for being located at or behind an ear of a user and an ITE-part (ITE) adapted for being located in or at an ear canal of a user's ear and comprising an output transducer (SPK), e.g. a receiver (loudspeaker). The BTE-part and the ITE-part are connected (e.g. electrically connected) by a connecting element (IC) comprising a connector (CON) and internal wiring in the ITE- and BTE-parts (cf. e.g. schematically illustrated as wiring Wx in the BTE-part). The BTE and ITE parts each comprise a separate housing enclosing the components of the part in question. FIGS. 1B, 2B, 3B, and 4B, each show the connecting element (IC) and the ITE-part (ITE) of the corresponding embodiments of the hearing devices of FIGS. 1A, 2A, 3A, and 4A in further detail. The BTE-parts of the embodiments of FIGS. 1B, 2B, 3B, and 4B each comprises a connector ($CON_{BTE}$) configured to match a connector ($CON_{IC}$) of the connecting element (IC).

The BTE- and ITE-parts of FIGS. 1A, 1B, 2A, 2B and 4A, 4B, each comprises one or more input transducers, e.g. microphones ($M_{BTE1}$, $M_{BTE2}$, and one or both of $M_{ITE1}$, $M_{ITE2}$, respectively), which are used to pick up sounds (S) from the environment of a user wearing the hearing device (HD). The ITE-part may be relatively open (cf. FIG. 1A, 2A, 3A) allowing air to pass through and/or around it thereby minimizing the occlusion effect perceived by the user (but also allowing sound to leak from the loudspeaker to the environment). The ITE-part may be less open than a typical RITE-style ITE-part, which comprises only a loudspeaker (SPK) and a dome (DO) to position the loudspeaker in the ear canal. In an embodiment, the ITE-part according to the present disclosure comprises a mould (MOULD) and is intended to allow a relatively large sound pressure level to be delivered to the ear drum of the user (e.g. a user having a severe-to-profound hearing loss), cf. e.g. FIG. 4A, e.g. comprising a ventilation channel to minimize occlusion.

In the embodiments of a hearing device (HD) shown in FIG. (1A, 1B)-(4A, 4B), the BTE-part (BTE) comprises two input transducers (e.g. microphones) ($M_{BTE1}$, $M_{BTE2}$) each for providing an electric input audio signal representative of an input sound signal. The BTE-parts of these embodiments each further comprises two (e.g. individually selectable) wireless receivers ($WLR_1$, $WLR_2$) for providing respective directly received auxiliary audio input and/or control or information signals from other devices, e.g. a remote control, a telephone, a microphone unit, an entertainment device, another hearing device, etc. The BTE-part comprises a substrate SUB whereon a number of electronic components (MEM, FE, DSP) are mounted. The BTE-part comprises a configurable signal processor (DSP) and memory (MEM) accessible therefrom. The signal processor (DSP) may form part of an integrated circuit, e.g. a (mainly) digital integrated circuit.

The hearing device (HD) of the embodiments of FIGS. 1A, 1B, 2A, 2B, 3A, 3B and 4A, 4B comprises an output transducer (SPK), located in the ITE-part (ITE), providing an enhanced output signal as stimuli (here acoustic vibrations in air) perceivable by the user as sound based on an enhanced audio signal from the signal processor (DSP) or a signal derived therefrom.

The ITE-part of the embodiments of FIGS. 1A, 2A, 3A and 4A further comprises a guiding element, e.g. a dome or mould (MOULD in FIG. 4A) or micro-mould (DO in FIG. 1A, 2A, 3A) for guiding and positioning the ITE-part in the ear canal (Ear canal) of the user.

In the scenario of FIGS. 1A, 2A, 3A and 4A, a (far-field) (target) sound source S is propagated (and mixed with other sounds of the environment) to respective sound fields $S_{BTE}$ at the BTE microphone ($M_{BTE1,2}$) of the BTE-part, $S_{ITE}$ at the ITE microphone(s) ($M_{ITE1,2}$) of the ITE-part, and $S_{ED}$ at the ear drum (Ear drum).

Each of the hearing devices (HD) exemplified in FIGS. 1A, 2A, 3A and 4A represents a portable (easily wearable) device, e.g. a hearing aid, and further comprises a battery (BAT), e.g. a rechargeable battery, for energizing electronic components of the BTE- and ITE-parts.

The embodiments of a hearing device (HD) exemplified in FIGS. 1A, 2A, 3A and 4A, e.g. a hearing aid (e.g. the processor (DSP) in FIGS. 1A, 2A, 3A and 4A or (SPU) in FIGS. 1B, 2B, 3B and 4B), may be adapted to provide a frequency dependent gain and/or a level dependent compression and/or a transposition (with or without frequency compression) of one or frequency ranges to one or more other frequency ranges, e.g. to compensate for a hearing impairment of a user.

Figure 1B:
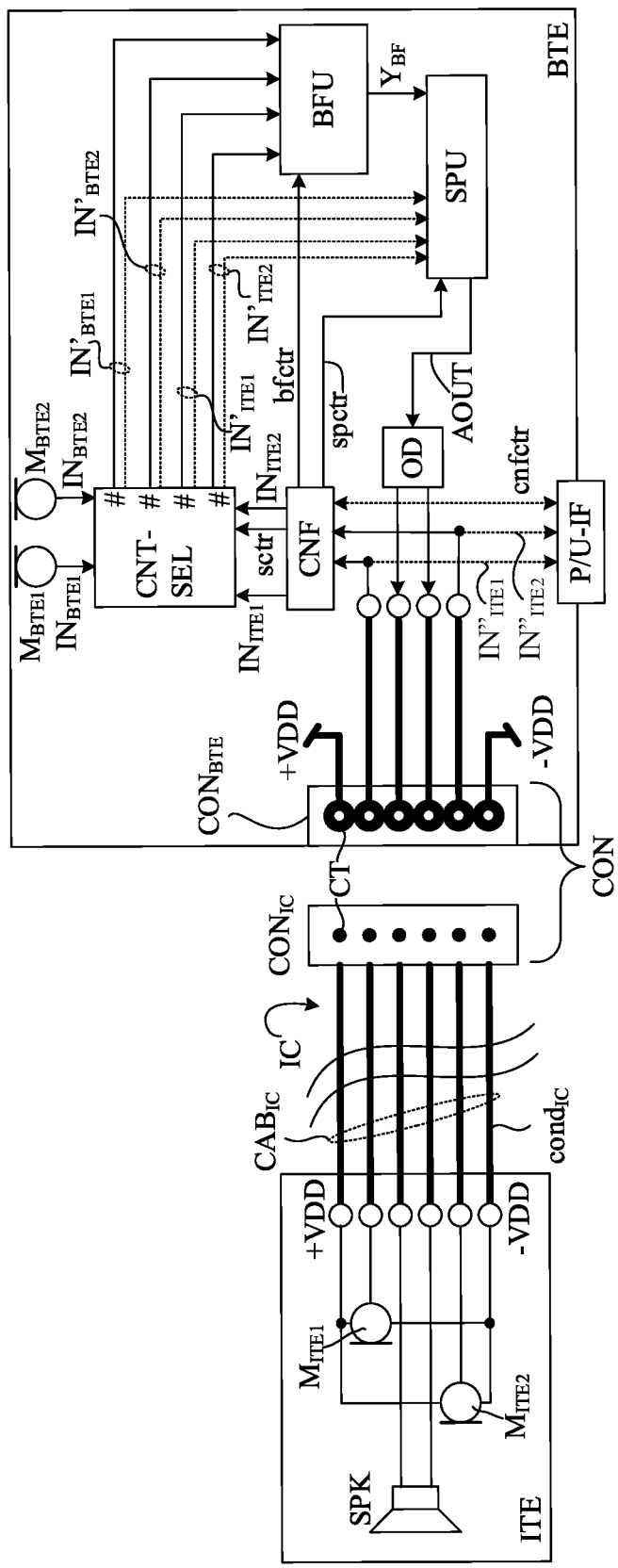
FIG. 1B shows a possible configuration of the hearing device in FIG. 1A.

The connecting element (IC) comprises a cable ($CAB_{IC}$) and a connector ($CON_{IC}$) (cf. FIG. 1B, 2B, 3B, 4B). The connector ($CON_{IC}$) comprises a multitude $N_T$ of electric termination elements (CT), e.g. pins or conducting strips on a carrier, (e.g. as here $N_T$=6 pins). The cable comprises a multitude $N_C$ of conductors ($cond_{IC}$), e.g. $N_C \geq 4$ (e.g. as here $N_C$=6). In the embodiments shown in the present disclosure, the connector is located at an end of the connecting element (IC) interfacing to the BTE-part (e.g. integrated with the housing of the BTE-part). The connector may, however, be located at the interface to the ITE-part instead, or a connector may be located at both ends. The cable may be of variable length according to the application in question, e.g. dependent on the user (as indicated by the two curved lines crossing the conductors). In the specific embodiments of FIG. 1B, 2B, 3B, 4B, two electric termination elements (CT) are allocated to supply voltages (+$V_{DD}$, −$V_{DD}$), two are allocated to drive the loudspeaker (SPK) (from the BTE-part), and two are allocated to transfer outputs from the (possible) two sensors of the ITE-part, e.g. microphones ($M_{ITE1}$, $M_{ITE2}$) or sensors ($S_{ITE1}$, $S_{ITE2}$). When one or both sensors are absent, the corresponding electric termination element(s) (CT) of the connector ($CON_{IC}$) of the connecting element (IC) is/are connected to a known (easily detectable) signal, here to one of the supply voltages (+$V_{DD}$, −$V_{DD}$), see e.g. FIG. 2B, 3B. In the BTE-part the electric termination elements (CT) of the connector ($CON_{BTE}$) of the BTE-part are electrically connected to relevant electric units. The two supply voltage termination elements (+$V_{DD}$, −$V_{DD}$) are connected to the battery (cf. BAT in FIG. 1A, 2A, 3A, 4A) (e.g. via an appropriate voltage controller) delivering said voltages. The two loudspeaker driver termination elements are connected to an output driver (OD) in the BTE-part providing processed signals representing sound (provided by signal processor SPU via audio signal AOUT). The two sensor termination elements are connected to configuration extractor (CNF) (either located in the hearing device (as shown in FIGS. 1B. 2B, 3B and 4B) or in a programming device connected to the hearing device via a programming interface (P-IF), cf. FIG. 1B and FIG. 7A, 7B).

As illustrated in FIGS. 1B, 2B, 3B and 4B, the BTE-part comprises two microphones ($M_{BTE1}$, $M_{BTE2}$) and a selector (CNT-SEL) receiving inputs ($IN_{BTE1}$, $IN_{BTE2}$) from the BTE-microphones and inputs ($IN_{ITE1}$, $IN_{ITE2}$) from a configuration and extraction unit (CNF). The selector (CNT-SEL) is configured to provide an appropriate routing of the input signals from the microphones and possible other sensors to a beamformer filter (BFU) and to a signal processor (SPU). Each of the inputs to the selector (CNT-SEL) can be routed either to the beamformer filter (BFU) or to the signal processor (SPU), cf. output signals ($IN'_{BTE1}$, $IN'_{BTE2}$, $IN'_{ITE1}$, $IN'_{ITE2}$) from the selector. The actual routing of the output signals from the selector is indicated by the solid lines and dotted lines, respectively, from the selector to the beamformer filter and the signal processor (cf. pairs of one solid and one dotted line for each output signal, indicating that the signal in question is routed either to the beamformer filter or to the signal processor). In other embodiments one or more of the signals may be routed to the beamformer filter as well as to the signal processor. The actual routing is controlled by control signal sctr from the configuration extractor (CNF), which also informs the beamformer filter (BFU) and the signal processor (SPU) about the current routing via control signals bfctr and spctr. The beamformer (BFU) provides one or more beamformed signals $Y_{BF}$ based on the currently selected input (microphone signals). The signal processor (SPU) processes the beamformed signal (e.g. according to a user's hearing impairment), possibly based on one or more further sensor signals according to the current configuration of the ITE-part and the current routing of the input signals ($IN'_{BTE1}$, $IN'_{BTE2}$, $IN'_{ITE1}$, $IN'_{ITE2}$).

Figure 5:
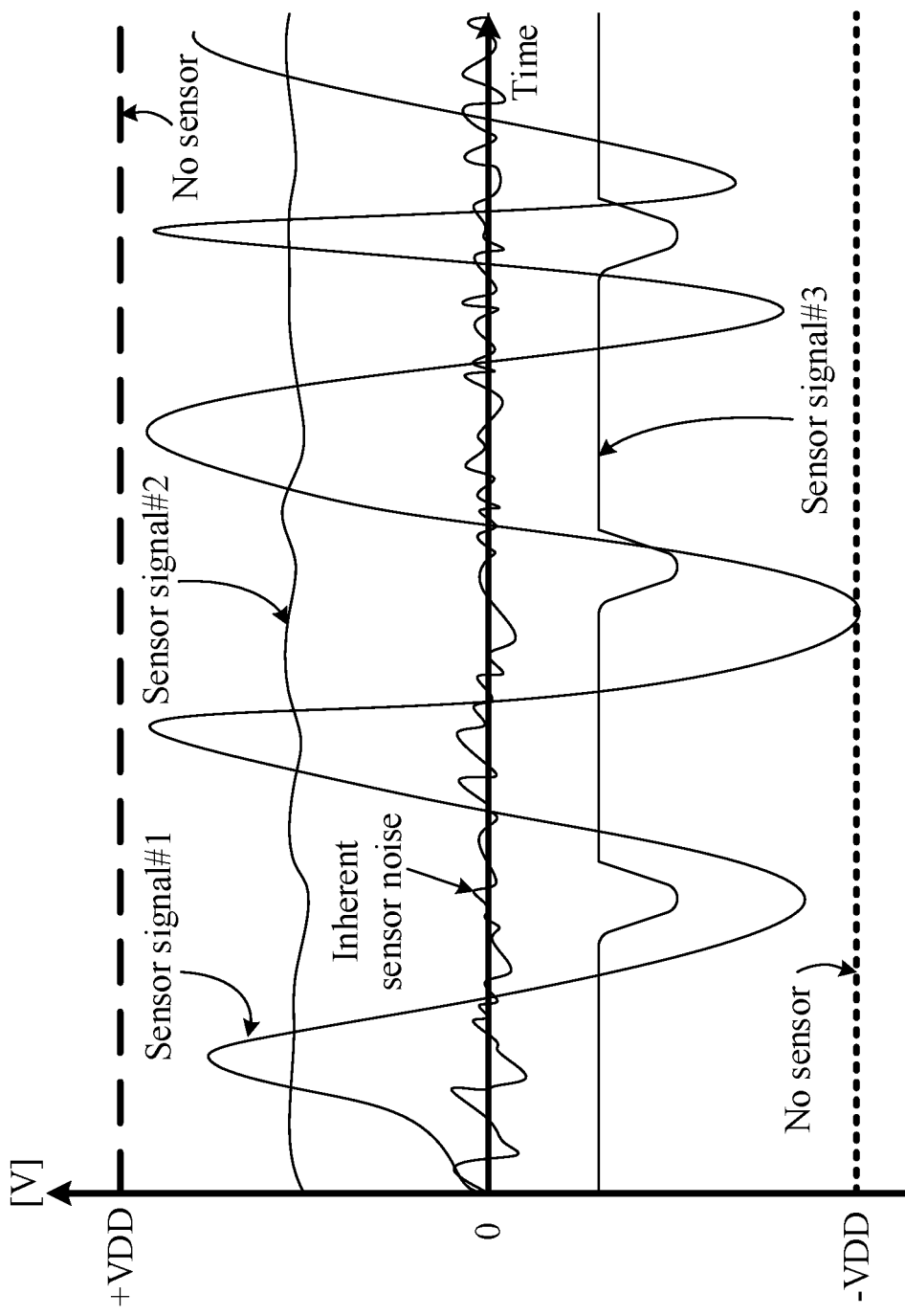
FIG. 5 shows exemplary output signals from sensor termination elements of an embodiment of a hearing device according to the present disclosure.

In FIGS. 1B. 2B, 3B and 4B, the sensor signals $IN''_{ITE1}$ and $IN''_{ITE2}$ from the ITE-sensors (microphones and/or other sensors, respectively) received via the connector ($CON_{BTE}$), are fed to the configuration extraction unit (CNF), where it is identified that the two sensor signals $IN''_{ITE1}$ and $IN''_{ITE2}$ represent respective first and second sensors, and in particular first and second microphones. The identification may (as schematically indicated in FIG. 5) be simply performed by first checking whether or not the input signals represent a known (predefined signal), here one of the supply voltages ($-V_{DD}$ and $+V_{DD}$). If yes, the sensor in question is not connected. If not, as here, and no other sensors than microphones are possible for the use case in question, it may be concluded that the microphones are connected. If not, as here, and indeed other sensors than microphones are possible for the use case in question, known (predefined) characteristic of the possible sensors may be identified in the configuration extraction unit (CNF) and based thereon it can be concluded which kind of sensor is present. In an embodiment, only one type of sensor other than a microphone is possible. In another embodiment, only two types of sensors other than a microphone are possible. Based on a predefined table of the possible combinations of sensors (microphones and other sensors) (cf. FIG. 6) and their possible output characteristics (e.g. average output level, basic noise level, frequency content, etc.) (cf. FIG. 6) and the intended use (internal coupling) of each sensor in the BTE-part, appropriate control signals can be applied to the selector (CNT-SEL, signal sctr), to the beamformer filter (BFU, signal bfctr) and to the signal processor (SPU, signal spctr).

The ITE-part of the embodiments of FIG. 1A, 1B, 2A, 2B, 4A, 4B comprises one (cf. $M_{ITE1}$ in FIG. 2A, 2B, 4A, 4B) or two (cf. $M_{ITE1}$, $M_{ITE2}$ in FIG. 1A, 1B) input transducers (e.g. microphone(s)) for picking up a sound ($S_{ITE}$) from the environment. The input transducer(s) cf. $M_{ITE1}$, $M_{ITE2}$)) located in the ITE-part are—depending on the acoustic environment—prone to pick up more sound from the output transducer (SPK) (i.e. unintentional acoustic feedback) than the input transducers ($M_{BTE1}$, $M_{BTE2}$) located in the BTE-part.

EXAMPLE 1 (FIG. 1A, 1B)

The ITE-Part Contains Two Microphones (and No Other Sensors)

CONF #3 in FIG. 6

The hearing device of FIG. 1A contains four input transducers ($M_{BTE1}$, $M_{BTE2}$ and $M_{ITE1}$), $M_{ITE2}$), e.g. microphones, two ($M_{ITE1}$, $M_{ITE2}$) in the ITE-part are located in or at the ear canal of a user and the other two ($M_{BTE1}$, $M_{BTE2}$) in the BTE-part are located elsewhere at the ear of the user (e.g. behind the ear (pinna) of the user), when the hearing device is operationally mounted on the head of the user. In the embodiment of FIG. 1A, the hearing device is configured to provide that three of the four input transducers ($M_{BTE1}$, $M_{ITE1}$ and $M_{ITE2}$) are located along a substantially horizontal line when the hearing device is mounted at the ear of the user in a normal, operational state (cf. double arrowed, dashed line OL in FIG. 1A). This has the advantage of facilitating beamforming of the electric input signals from the input transducers in an appropriate (horizontal) direction, e.g. in the 'look direction' of the user (e.g. towards a target sound source) and/or allowing a beamformer to be constructed for cancelling feedback from the loudspeaker reflected by the eardrum back to the input transducers ($M_{ITE1}$, $M_{ITE2}$), cf. e.g. EP2843971A1. The fourth input transducer ($M_{BTE2}$) is located out of the horizontal plane, but is still being used for beamforming (which may be relevant to be able to adapt to out of plane sound sources (e.g. above or below the head of the user)).

FIG. 1B illustrates the embodiment of a hearing device shown in FIG. 1A. In this configuration, the (maximum) two sensors of the ITE-part are microphones ($M_{ITE1}$, $M_{ITE2}$). Hence, if both microphones are functioning and appropriately connected, their output signals will provide an electric signal in a predefined range (here between $-V_{DD}$ and $+V_{DD}$) as indicated in FIG. 5, either as microphone noise (cf. Inherent sensor noise in FIG. 5), if no acoustic signal is present, or as an ordinary time varying microphone signal, if a sound signal (e.g. a test signal or background speech and/or noise) is present (e.g. Sensor signal #1 in FIG. 5). In the embodiment of FIG. 1B, it is concluded that two microphones are present, and the corresponding microphone signals are fed to the selector (CNT-SEL) together with the selector control signal (sctr). The selector (CNT-SEL) receives the signals ($IN_{ITE1}$, $IN_{ITE2}$) from the configuration extraction unit (CNF) and the BTE-microphone signals ($IN_{BTE1}$, $IN_{BTE2}$) from the BTE-microphones ($M_{BTE1}$, $M_{BTE2}$). The selector (CNT-SEL) is configured to be controlled by the selector control signal (sctr) to allow selection of an appropriate routing of the input sensor signals (here, $IN_{BTE1}$, $IN_{BTE2}$, $IN_{ITE1}$, $IN_{ITE2}$). The appropriate routing for a given sensor configuration may e.g. be read from a table (cf. e.g. FIG. 6) stored in a memory of the hearing device (e.g. in the processor SPU) accessible to the configuration extractor (CNF). The appropriate routing (or at least the configuration of microphones to be used in by the beamformer filter) is communicated to the beamformer filter and to the signal processor (or at least the kind or sensor signals that are to be used by the processor) by the respective control signals (bfctr, spctr). The appropriate routing is indicated by the solid lines of signals $IN'_{BTE1}$, $IN'_{BTE2}$, $IN'_{ITE1}$ and $IN'_{ITE2}$ to the beamformer filter (BFU) and thus no signals to the signal processor (SPU). In other words, the signals from both of the BTE-microphones ($M_{BTE1}$, $M_{BTE2}$) and the two ITE-microphones are used for creating appropriate beamformed signals. In another embodiment, one of BTE-microphones (e.g. $M_{BTE2}$) may be used as a sensor (e.g. to provide a separate level detector, e.g. using another type of microphone, or aiming at some other purpose) instead of or in addition to being used for beamforming.

EXAMPLE 2 (FIG. 2A, 2B)

The ITE-Part Contains One Microphone (and No Other Sensors)

CONF #2 in FIG. 6

Figure 2A:
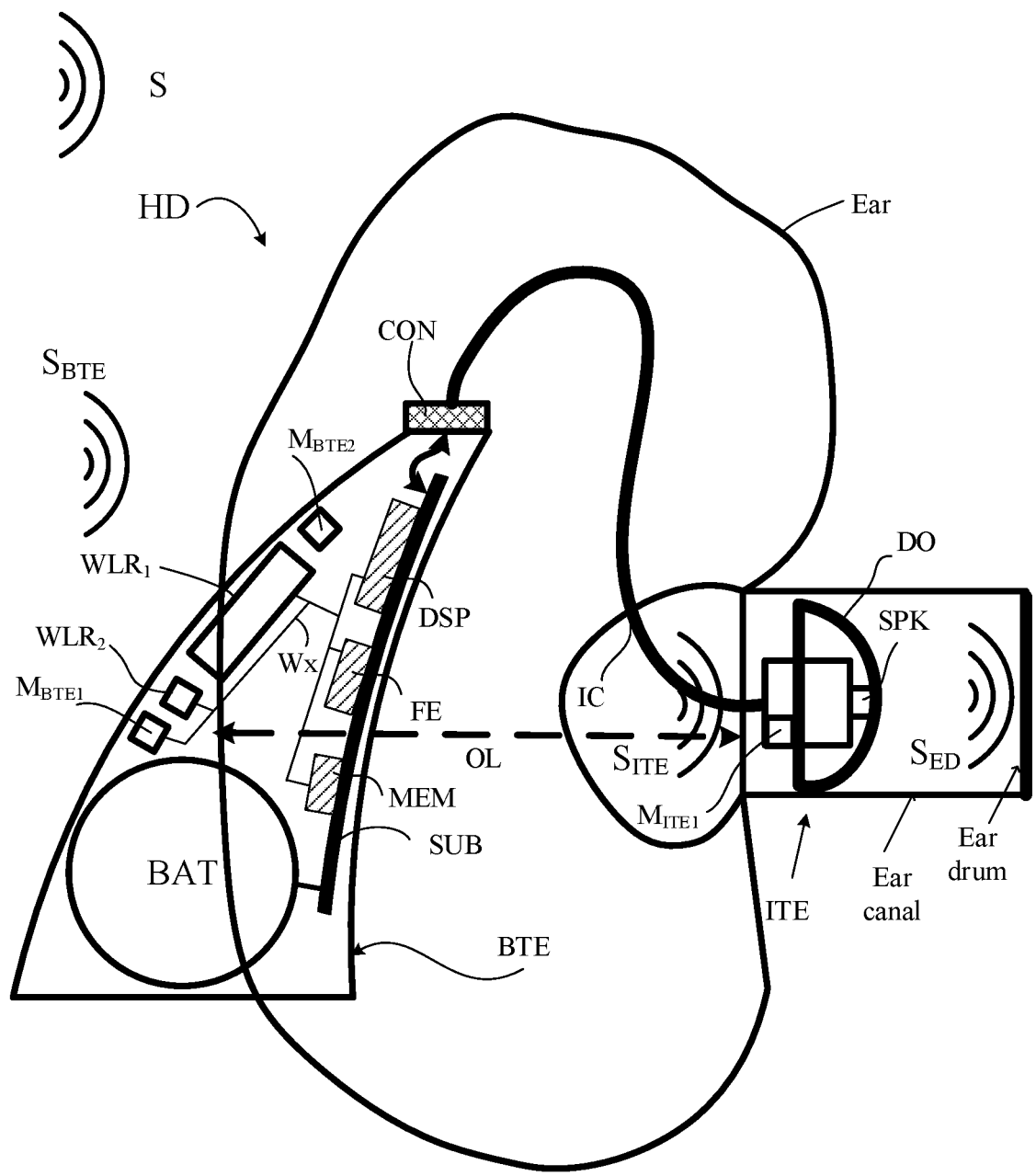
FIG. 2A shows a second embodiment of a hearing device comprising a BTE-part and an ITE-part according to the present disclosure.
Figure 2B:
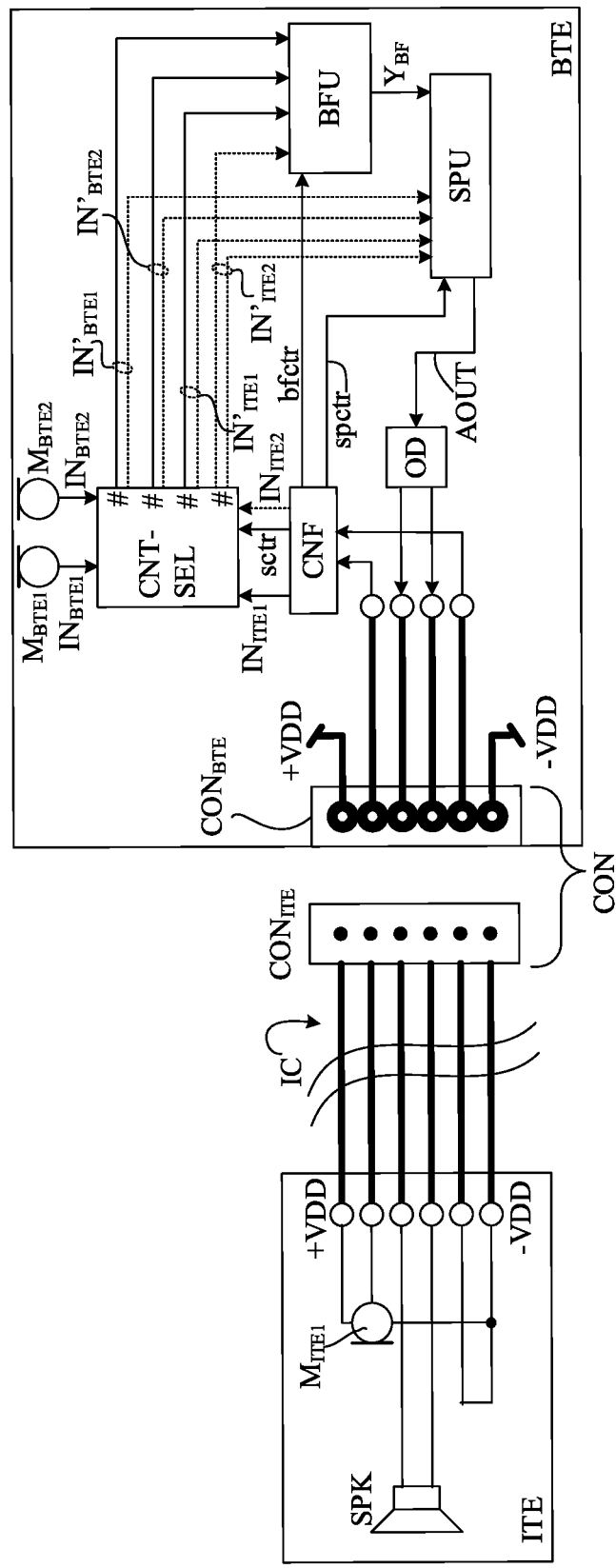
FIG. 2B shows a possible configuration of the hearing device in FIG. 2A.

The embodiment of a hearing device shown in FIGS. 2A and 2B is largely identical to the embodiment shown in FIG. 1A, 1B except for the following differences. The embodiment of a hearing device shown in FIG. 2A, 2B comprises three input transducers ($M_{BTE1}$, $M_{BTE2}$, $M_{ITE1}$) (instead of four in FIG. 1A, 1B). The only difference is that instead of two ITE-microphones, only one is present ($M_{ITE1}$) is present in the ITE-part. As appears from FIG. 2B, the embodiment of FIG. 2A, 2B does not comprise a further sensor (in other words, the sensor position and corresponding electric termination elements (CT) of the connector ($CON_{IC}$) (and connected cable conductor) is unused (void) and instead connected to the negative supply voltage $-V_{DD}$ for easy identification in the configuration extractor (CNF). As also appears from FIG. 2B, all three microphone signals ($IN_{BTE1}$, $IN_{BTE2}$, $IN_{ITE1}$) are routed to the beamformer filter BFU and used for providing one or more beamformed signals $Y_{BF}$ for further processing in the signal processor (SPU).

EXAMPLE 3 (FIG. 3A, 3B)

The ITE-Part Contains No Microphones (and No Other Sensors)

CONF #1 in FIG. 6

Figure 3A:
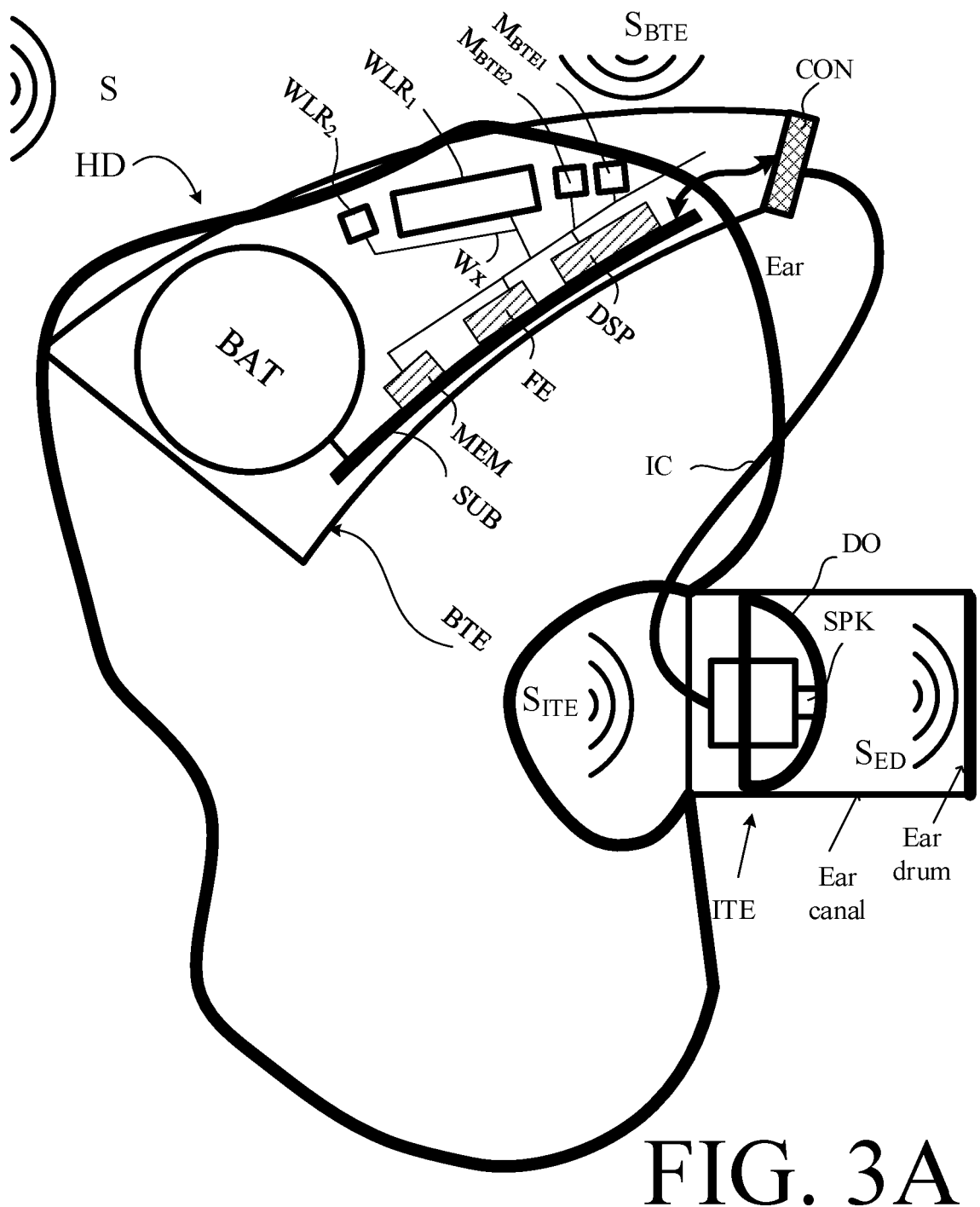
FIG. 3A shows a third embodiment of a hearing device comprising a BTE-part and an ITE-part according to the present disclosure.
Figure 3B:
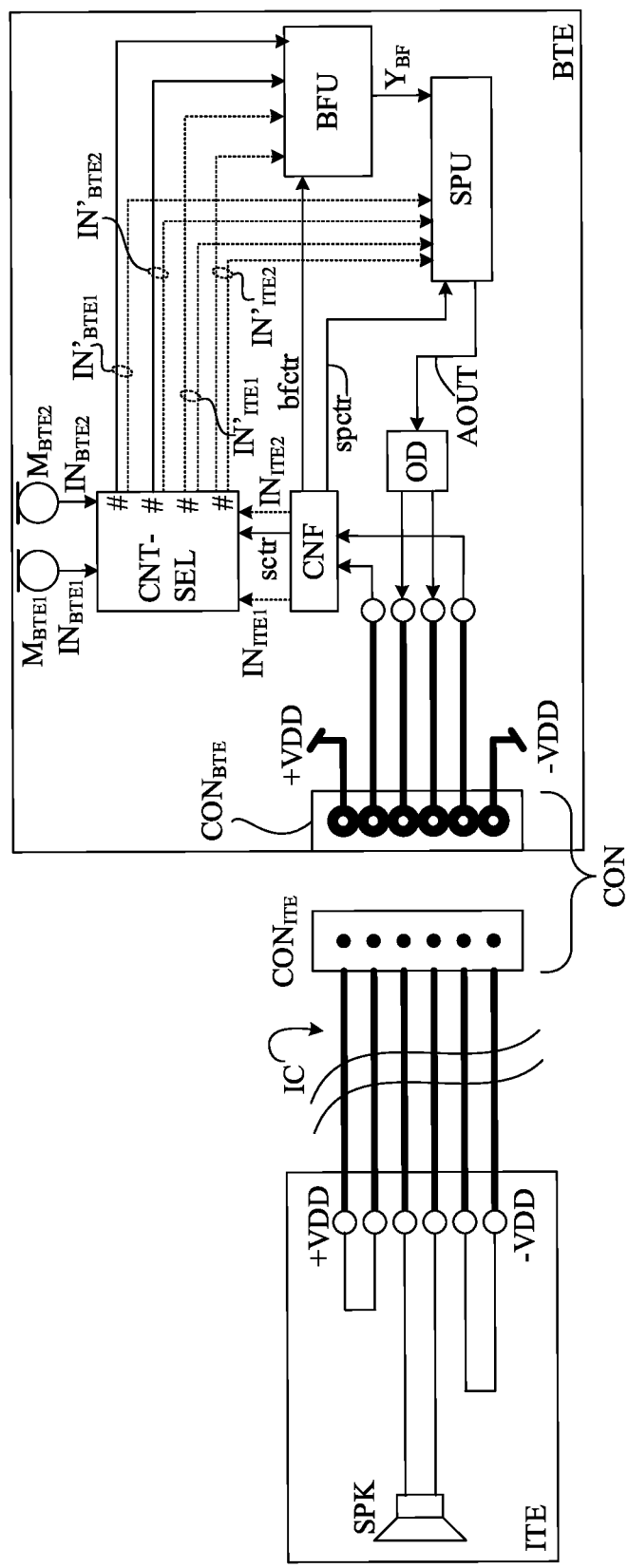
FIG. 3B shows a possible configuration of the hearing device in FIG. 3A.

The embodiment of a hearing device shown in FIGS. 3A and 3B is largely identical to the embodiment shown in FIG. 2A, 2B except for the following differences. As appears from FIG. 3A, the two BTE-microphones ($M_{BTE1}$, $M_{BTE2}$) are located in the top part of the BTE-part instead of along the line OL in FIGS. 1A and 2A. In the embodiment of FIG. 3A, 3B, the two BTE-microphones ($M_{BTE1}$, $M_{BTE2}$) of the BTE-part are located in a typical state of the art BTE manner, so that—during wear of the hearing device—the two microphones are positioned along a horizontal line pointing substantially in a look direction of the user at the top of pinna (whereby the two microphones in FIG. 3A can be seen as 'front' ($M_{BTE1}$) and 'rear' ($M_{BTE2}$) microphones, respectively). As appears from FIG. 3B, the embodiment of FIG. 3A, 3B neither comprises a microphone, nor a further sensor (in other words, the two sensor positions and corresponding electric termination elements (CT) of the connector ($CON_{IC}$) (and connected cable conductor) are unused (void) and instead connected to the negative supply voltage $-V_{DD}$ and positive supply voltages, respectively, for easy identification in the configuration extractor (CNF). In the embodiment of FIG. 2B, the unused sensor termination elements are connected to different supply voltages. They may instead be connected to the same voltage, e.g. $-V_{DD}$ (or in another embodiment to Ground), or to a known (easily generated and identified) signal. As also appears from FIG. 3B, the two microphone signals ($IN_{BTE1}$, $IN_{BTE2}$) are routed to the beamformer filter BFU and used for providing one or more beamformed signals $Y_{BF}$ for further processing in the signal processor (SPU).

EXAMPLE 4 (FIG. 4A, 4B)

The ITE-Part Contains One Microphone and One Other Sensor

CONF #4 in FIG. 6

Figure 4A:
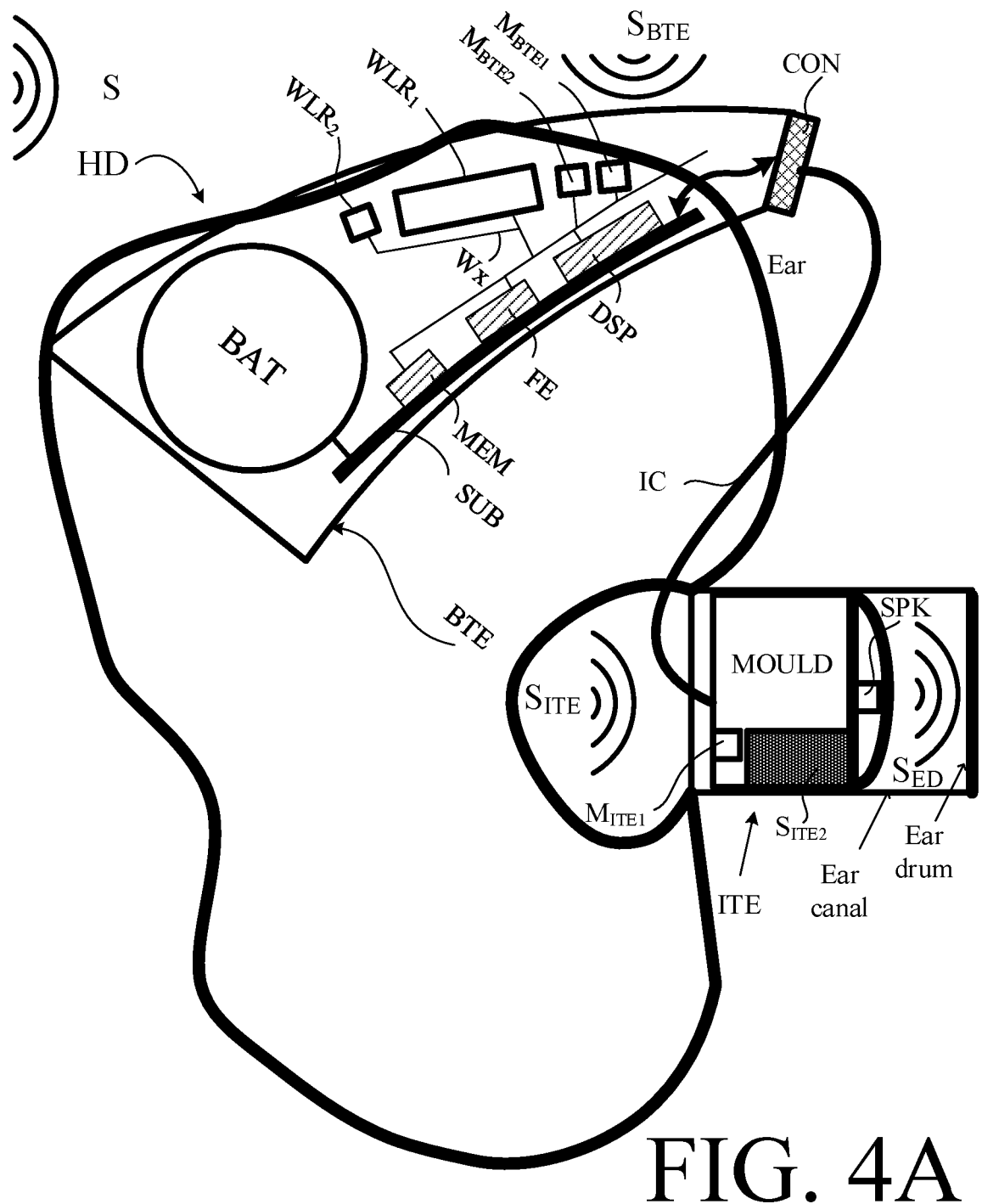
FIG. 4A shows a fourth embodiment of a hearing device comprising a BTE-part and an ITE-part according to the present disclosure.
Figure 4B:
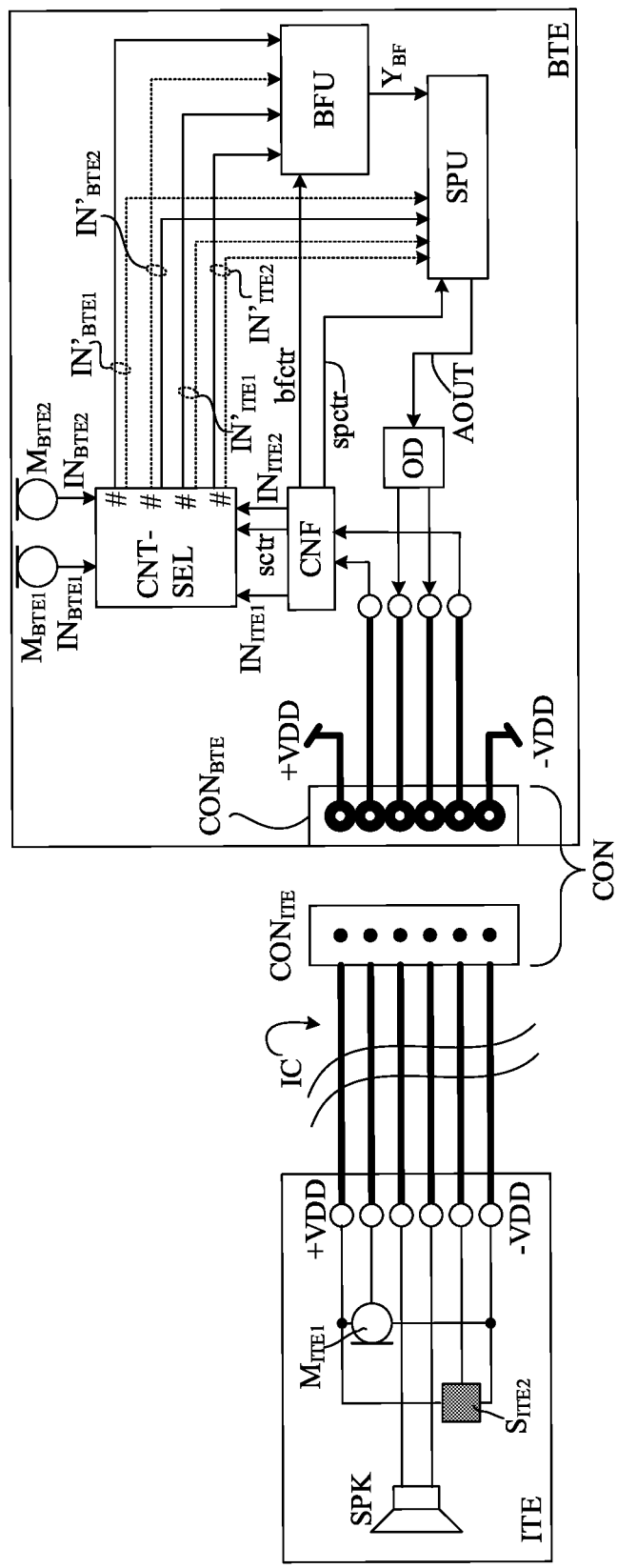
FIG. 4B shows a possible configuration of the hearing device in FIG. 4A.

The embodiment of a hearing device shown in FIGS. 34A and 4B is largely identical to the embodiment shown in FIG. 3A, 3B except for the following differences. As appears from FIG. 4A, the ITE-part comprises a microphone $M_{ITE1}$, and a further sensor $S_{ITE2}$. The ITE-part comprises an ear mould, e.g. adapted to the user's ear canal to minimize leakage of sound from the loudspeaker (SPK) of the hearing device to the environment (and from the environment to the ear drum). The mould may comprise a vent to allow pressure to be aligned between the environment and the residual volume between the mould and the ear drum (to minimize occlusion). The further sensor is located in the ITE-part near the surface of the housing allowing a contact or interaction with tissue of the ear canal. The sensor may e.g. be a sensor of body signals, e.g. a light sensitive sensor (e.g. a PPG sensor) or an electric potential sensor (e.g. to pick up signals from the brain (e.g. EEG) or and/from the eye balls (e.g. EOG) or from muscle contractions (e.g. jaw movements).

As appears from FIG. 4B, in the embodiment of FIG. 4A, 4B, the three microphone signals ($IN_{BTE1}$, $IN_{BTE2}$, $IN_{ITE1}$) are routed to the beamformer filter BFU and used for providing one or more beamformed signals $Y_{BF}$ for further processing in the signal processor (SPU), whereas the further sensor signal ($IN_{ITE2}$) is routed to the signal processor (SPU) for being considered there, (e.g. for being processed and/or transmitted to another device, e.g. to a user interface for presentation there).

The programming interface (P-IF) and user communication interface (U-IF) are only shown in the embodiment of FIG. 1B, but may as well be included in the embodiments of FIGS. 2B, 3B and/or 4B. The programming interface and the user communication interface may be implemented using one or both wireless transceivers (WLR1, WLR2) shown in FIG. 1A, 2A, 3A, 4A. Alternatively, the interfaces may be implemented as wired connections, e.g. via a connector.

FIG. 5 shows exemplary output signals from sensor termination elements of an embodiment of a hearing device according to the present disclosure. Signals are shown as voltage [V] versus time. Unused sensor termination elements are connected to a constant voltage, e.g. −VDD or +VDD. An Inherent sensor noise (e.g. shot noise) is illustrated as an exemplary sensor output in case of absence of a normal sensor input. The Inherent sensor noise may be characterised for a given sensor in advance of use of the hearing device and used by the configuration extractor to determine a given kind of sensor (alone or in combination with other information). Two characteristic sensor outputs (denoted Sensor signal #1, Sensor signal #2, and Sensor signal #3, respectively) are schematically illustrated. The oscillating (AC) Sensor signal #1 may e.g. represent an output from a microphone. The relatively stable (DC) Sensor signal #2 may e.g. represent an output from a temperature sensor. The periodic Sensor signal #3 may e.g. represent an output from a heart rate sensor. Time scales for the different sensor signals may be different. Instead of characteristics of the time domain signal, characteristics of the frequency spectrum may be relied on for identifying the kind of sensor(s) presently being connected to the first hearing device part.

FIG. 6 shows a table listing possible combinations of sensors in the form of microphones and other sensors for an exemplary ITE part of a hearing device according to the present disclosure, and corresponding configuration control indicators. Six different configurations (denoted CONF #1 to CONF #6) of an ITE-part having space for one loudspeaker and two sensors are listed. All configurations comprise a loudspeaker. This need not necessarily be the case, though.

CONF #1 is illustrated in FIG. 3A, 3B: The beamformer control signal bfctr is indicated as bfctr=0 (no further microphone signals, in addition to the two BTE-microphone signals). The processor control signal spctr is indicated as spctr=0 (no further sensor signals are available).

CONF #2 is illustrated in FIG. 2A, 2B: The beamformer control signal bfctr is indicated as bfctr=1 (one ITE-microphone signal is routed to the beamformer filter, in addition to the two BTE-microphone signals). The processor control signal spctr is indicated as spctr=0 (no further sensor signals are available).

CONF #3 is illustrated in FIG. 1A, 1B: The beamformer control signal bfctr is indicated as bfctr=2 (two ITE-microphone signals are routed to the beamformer filter, in addition to the two BTE-microphone signals). The processor control signal spctr is indicated as spctr=0 (no further sensor signals are available).

CONF #4 is illustrated in FIG. 4A, 4B: The beamformer control signal bfctr is indicated as bfctr=1 (one ITE-microphone signal is routed to the beamformer filter, in addition to the two BTE-microphone signals). The processor control signal spctr is indicated as spctr=1 (one further sensor signal is available and routed to the signal processor).

CONF #5: The beamformer control signal bfctr is indicated as bfctr=0 (no further microphone signals are routed to the beamformer filter, in addition to the two BTE-microphone signals). The processor control signal spctr is indicated as spctr=1 (one further sensor signal is available and routed to the signal processor).

CONF #6: The beamformer control signal bfctr is indicated as bfctr=0 (no further microphone signals are routed to the beamformer filter, in addition to the two BTE-microphone signals). The processor control signal spctr is indicated as spctr=2 (two further sensor signals are available and routed to the signal processor).

Other configurations are possible for ITE-parts where more sensor positions are available. For such ITE-parts, either a connecting element with more electric conductors and associated electric termination elements is needed, or an ITE-part that is configured to share the electric conductors and associated electric termination elements between two or more sensors. This may be appropriate for sensors form monitoring parameters or properties that do not need to be constantly recorded.

As indicated in FIG. 1B, the sensor signals ($IN''_{ITE1}$, $IN''_{ITE2}$) from the sensors in the ITE-part may be routed to a programming interface (P-IF) and/or to a user communication interface (U-IF) for evaluation and/or display. In an embodiment, the configuration extractor (CNF) is located in a programming device (PD), e g running a fitting software, connected to the hearing device via the programming interface (P-IF). The configuration extractor (CNF) may be configured to receive a control signal (cnfctr) from a programming device (PD) and/or from an auxiliary device (AD) implementing a user interface (UI) for the hearing device. Likewise, the configuration extractor (CNF) may be configured to transmit a control signal (cnfctr) indicative of a current configuration of the ITE-part to the programming device (PD) (cf. e.g. FIG. 7B) and/or to the auxiliary device (AD) implementing a user interface (UI) for the hearing device (cf. e.g. FIG. 7C). The same configuration (allowing communication between the hearing device and a programming device (PD) and/or another device (AD)) may be implemented in the other embodiments of a hearing device according to the present disclosure.

Figure 7A:
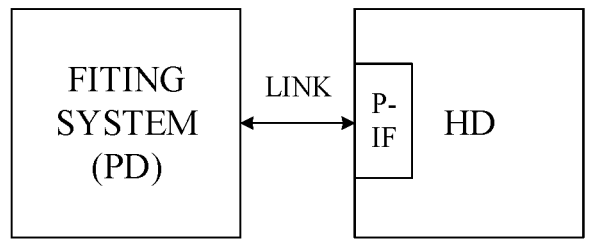
FIG. 7A shows a first embodiment of a hearing system comprising a programming device and a hearing device according to the present disclosure.

FIG. 7A shows a first embodiment of a hearing system (HS) comprising a programming device (PD) and a hearing device (HD) according to the present disclosure. The programming device (PD) implements a fitting system for configuring the hearing device (HD) according to the needs of a user (e.g. to compensate for a hearing impairment). The programming device (PD) and a hearing device (HD) are connected by a communication link (Link) via the programming interface (P-IF) of the hearing device.

Figure 7B:
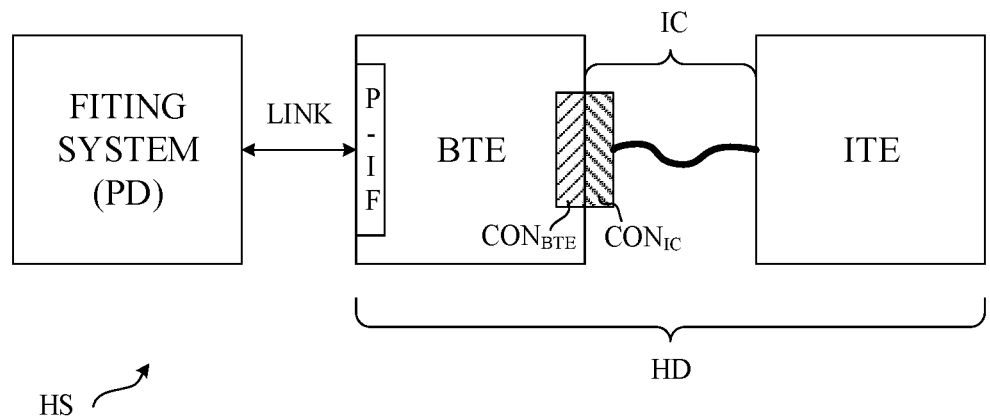
FIG. 7B shows a second embodiment of a hearing system comprising a programming device and a hearing device according to the present disclosure.

FIG. 7B shows a second embodiment of a hearing system (HS) comprising a programming device (PD) and a hearing device (HD) according to the present disclosure. The hearing device comprises two separate parts, a BTE-part (BTE) and an ITE-part (ITE) that are electrically connected by the connecting element (IC) comprising a cable and a connector ($CON_{IC}$, $CON_{BTE}$) as described in connection with FIGS. 1A, 1B, 2A, 2B, 3A, 3B and 4A, 4B.

Figure 7C:
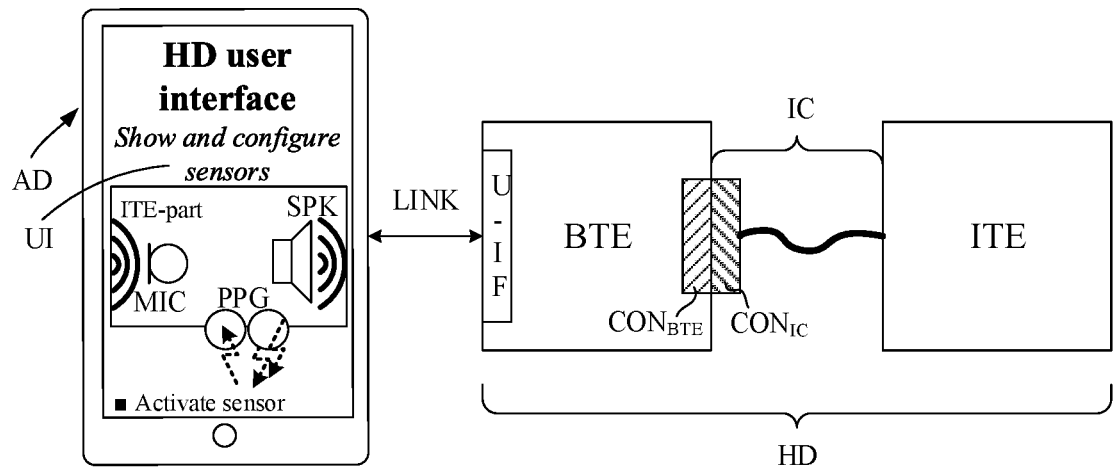
FIG. 7C shows an embodiment of a hearing system comprising an auxiliary device supporting a user interface for a hearing device and a hearing device according to the present disclosure.

FIG. 7C shows an embodiment of a hearing system (HS) comprising an auxiliary device (AD) supporting a user interface (UI) for a hearing device via a wired or wireless link (LINK) and user communication interface (U-IF) and a hearing device (HD) according to the present disclosure. The user interface may allow a user to see which sensors the ITE-part (ITE) comprises and how they are configured in the hearing device. The user interface may also allow the user to influence the configuration, e.g. to determine which microphones to be used for beamforming, to activate or deactivate a given sensor (e.g. by selecting the sensor and press Activate (Deactivate). The auxiliary device (AD) may be or comprise a remote control device. The user interface may e.g. be implemented as an APP of a smartphone or tablet computer or the like. An exemplary screen of the graphical user interface (UI) is illustrated in FIG. 7C. A present configuration of the ITE-part (ITE) is shown on the screen. The ITE-part comprises a loudspeaker (SPK), a microphone (MIC) and a PPG-sensor (PPG). The microphone and the PPG-sensor are activated. This may e.g. be helpful for a user having two (or more) different ITE-part for use at different occasions, e.g. one comprising two ITE-microphones for use during daytime wear of the hearing device (e.g. for beam-forming, and/or active noise cancellation), and another comprising one or two sensors, e.g. a PPG-sensor and/or an EEG-sensor, for use during night time wear of the hearing device (e.g. to monitor a sleeping pattern, e.g. a sleeping disorder, such as (obstructive) sleep 'apnoea', which may be detected by monitoring one or more of heart rate, brain activity, breathing patterns, muscle movements, and blood oxygen levels during sleep). A shift between the two ITE-parts may be configured (or just checked) using the graphical user interface (e.g. of a smartphone).

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein.

Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

EP2200347A2 (OTICON) 23.06.2010
US20170180882A1 (OTICON) 22.06.2017
WO2009065742A1 (OTICON, BERNAFON) 28.05.2009
EP2843971A1 (OTICON) 04.03.2015

The invention claimed is:

1. A hearing device adapted for being located at or in an ear of a user, the hearing device comprising
    first and second electrically connectable hearing device parts having separate first and second housings, at least the second hearing device part being one of a multitude of variants that are replaceably connectable to the first hearing device part, each variant providing different functionality to the hearing device,
    a connecting element configured to electrically connect the first hearing device part and the second hearing device part, the connecting element comprising
        an electric cable comprising a multitude of electric conductors,
        a first electric connector comprising a multitude of first electric termination elements electrically connected to said multitude of electric conductors, the first electric connector being configured to be mechanically and electrically joined with a matching second electric connector;
    the first or second hearing device part comprising
    said second electric connector, said second electric connector comprising a multitude of second electric termination elements electrically connected to electric components of the first or second hearing device part, respectively, and configured to electrically connect conductors of the cable with said electric components of the first and second hearing device parts when the first and second electric connectors are joined,
    the second hearing device part comprising
    a loudspeaker, and/or
    a number of sensors for sensing
        a current property of the environment of the hearing device; and/or
        a current state of the user wearing the hearing device,
    each of said number of sensors providing an electric sensor signal representative of a property of the environment or a state of the user, wherein said loudspeaker and/or said number of sensors are electrically connected to said first hearing device part via said connecting element,
    the first hearing device part comprising a configuration extractor electrically connected to said second hearing device part via said connecting element and adapted to identify, from signals outputted respectively from said number of sensors and received by the first hearing device part via said connecting element, a current configuration of sensors in said second hearing device part.

2. A hearing device according to claim 1 wherein said number of sensors comprises one or more of a microphone, a light-sensitive sensor, and a brainwave sensor.

3. A hearing device according to claim 1 wherein at least one of the electric conductors of the electric cable, at least in a specific mode of operation of the hearing device, is allocated for use by one of the number of sensors.

4. A hearing device according to claim 1 wherein each of the number of sensors is allocated a different one of the number of electric termination elements and associated electric conductors of the cable to transfer a respective electric sensor signal to the first hearing device part.

5. A hearing device according to claim 1 wherein at least one of the electric termination elements and associated electric conductors of the cable are allocated to a supply voltage or a voltage derived therefrom.

6. A hearing device according to claim 1 wherein at least one of said number of electric sensors provides an electric sensor signal having predetermined characteristics.

7. A hearing device according to claim 1 wherein at least one of the number of sensors has a digital output and is adapted to communicate an identifier of said sensor to the first hearing device part via its allocated conductor or a conductor dedicated to data, and wherein the configuration extractor is adapted to decode said identifier.

8. A hearing device according to claim 1 wherein at least one of the number of sensors has an analogue output, and wherein the configuration extractor is adapted to identify said sensor based on its intrinsic noise signal and/or on an output signal from the sensor reflecting its normal function.

9. A hearing device according to claim 1 wherein the second hearing device part is adapted to be located at least partially in an ear canal of the user.

10. A hearing device according to claim 9 wherein the number of sensors comprises a microphone intended to face the ear drum when the second hearing device part is located at or in an ear of the user, and wherein the configuration extractor is adapted to detect the user's heartbeat in the output signal from the microphone, and to thereby identify the sensor as an inward facing microphone.

11. A hearing device according to claim 1 configured to identify each of said number of sensors individually to thereby identify the current configuration of sensors in said second hearing device part.

12. A hearing device according to claim 1 configured to control the use of the number of sensors in the hearing device.

13. A hearing device according to claim 1 being constituted by or comprising a hearing aid, a headset, an earphone, an ear protection device or a combination thereof.

14. A hearing device according to claim 1 comprising a user communication interface, e.g. a wireless user communication interface, allowing a user to influence functionality of the hearing device via a user interface.

15. A hearing device adapted for being located at or in an ear of a user, the hearing device comprising
    first and second electrically connectable hearing device parts having separate first and second housings, at least the second hearing device part being one of a multitude of variants that are replaceably connectable to the first hearing device part, each variant providing different functionality to the hearing device, a connecting element configured to electrically connect the first hearing device part and the second hearing device part, the connecting element comprising
an electric cable comprising a multitude of electric conductors,
a first electric connector comprising a multitude of first electric termination elements electrically connected to said multitude of electric conductors, the first electric connector being configured to be mechanically and electrically joined with a matching second electric connector;
the first or second hearing device part comprising
said second electric connector, said second electric connector comprising a multitude of second electric termination elements electrically connected to electric components of the first or second hearing device part, respectively, and configured to electrically connect conductors of the cable with said electric components of the first and second hearing device parts when the first and second electric connectors are joined,
the second hearing device part comprising
a loudspeaker, and/or
a number of sensors for sensing
a current property of the environment of the hearing device; and/or
a current state of the user wearing the hearing device,
each of said number of sensors providing an electric sensor signal representative of a property of the environment or a state of the user, wherein said loudspeaker and/or said number of sensors are electrically connected to said first hearing device part via said connecting element,
the first hearing device part comprising a configuration extractor electrically connected to said second hearing device part via said connecting element and adapted to identify a current configuration of sensors in said second hearing device part,
wherein each of the number of sensors is allocated a different one of the number of electric termination elements and associated electric conductors of the cable to transfer a respective electric sensor signal to the first hearing device part, and
wherein an electric termination element and associated electric conductor of the cable, which is allocated to a specific one of the number of sensors, is supplied with a predefined signal, when said specific sensor is absent from said second hearing device part.

16. A hearing device adapted for being located at or in an ear of a user, the hearing device comprising
first and second electrically connectable hearing device parts having separate first and second housings, at least the second hearing device part being one of a multitude of variants that are replaceably connectable to the first hearing device part, each variant providing different functionality to the hearing device,
a connecting element configured to electrically connect the first hearing device part and the second hearing device part, the connecting element comprising
an electric cable comprising a multitude of electric conductors,
a first electric connector comprising a multitude of first electric termination elements electrically connected to said multitude of electric conductors, the first electric connector being configured to be mechanically and electrically joined with a matching second electric connector;
the first or second hearing device part comprising
said second electric connector, said second electric connector comprising a multitude of second electric termination elements electrically connected to electric components of the first or second hearing device part, respectively, and configured to electrically connect conductors of the cable with said electric components of the first and second hearing device parts when the first and second electric connectors are joined,
the second hearing device part comprising
a loudspeaker, and/or
a number of sensors for sensing
a current property of the environment of the hearing device; and/or
a current state of the user wearing the hearing device, each of said number of sensors providing an electric sensor signal representative of a property of the environment or a state of the user, wherein said loudspeaker and/or said number of sensors are electrically connected to said first hearing device part via said connecting element, the first hearing device part comprising a configuration extractor electrically connected to said second hearing device part via said connecting element and adapted to identify a current configuration of sensors in said second hearing device part,
wherein the number of sensors comprises a microphone, and wherein the hearing device is configured to play a test sound signal, and wherein the configuration extractor is adapted to detect the test sound signal in the feedback signal received by said microphone, and to thereby identify the sensor as a microphone.

17. A hearing device adapted for being located at or in an ear of a user, the hearing device comprising
first and second electrically connectable hearing device parts having separate first and second housings, at least the second hearing device part being one of a multitude of variants that are replaceably connectable to the first hearing device part, each variant providing different functionality to the hearing device,
a connecting element configured to electrically connect the first hearing device part and the second hearing device part, the connecting element comprising
an electric cable comprising a multitude of electric conductors,
a first electric connector comprising a multitude of first electric termination elements electrically connected to said multitude of electric conductors, the first electric connector being configured to be mechanically and electrically joined with a matching second electric connector;
the first or second hearing device part comprising
said second electric connector, said second electric connector comprising a multitude of second electric termination elements electrically connected to electric components of the first or second hearing device part, respectively, and configured to electrically connect conductors of the cable with said electric components of the first and second hearing device parts when the first and second electric connectors are joined,
the second hearing device part comprising
a loudspeaker, and/or
a number of sensors for sensing
a current property of the environment of the hearing device; and/or
a current state of the user wearing the hearing device,
each of said number of sensors providing an electric sensor signal representative of a property of the environment or a state of the user, wherein said loudspeaker and/or said number of sensors are electrically connected to said first hearing device part via said connecting element, the first hearing device part comprising a configuration extractor electrically connected to said second hearing device part via said connecting element and adapted to identify a current configuration of sensors in said second hearing device part, wherein the configuration extractor is adapted to compare an electric sensor signal from a particular sensor among said number of sensors before and after being located at or in an ear of a user, and based thereon to identify the particular sensor.

18. A hearing system comprising a hearing device and a programming device for configuring the hearing device, the hearing device comprising first and second electrically connectable hearing device parts having separate first and second housings, at least the second hearing device part being one of available in a multitude of variants that are replaceably connectable to the first hearing device part, each variant providing different functionality to the hearing device, a connecting element configured to electrically connect the first hearing device part and the second hearing device part, the connecting element comprising an electric cable comprising a multitude of electric conductors, a first electric connector comprising a multitude of first electric termination elements electrically connected to said multitude of electric conductors, the first electric connector being configured to be mechanically and electrically joined with a matching second electric connector;

the first or second hearing device part comprising said second electric connector, said second electric connector comprising a multitude of second electric termination elements electrically connected to electric components of the first or second hearing device part, respectively, and configured to electrically connect conductors of the cable with said electric components of the first and second hearing device parts when the first and second electric connectors are joined, the second hearing device part comprising a loudspeaker, and/or a number of sensors for sensing a current property of the environment of the hearing device; and/or a current state of the user wearing the hearing device, each of said number of sensors providing an electric sensor signal representative of a property of the environment or a state of the user, wherein said loudspeaker and/or said number of sensors are electrically connected to said first hearing device part via said connecting element, the first hearing device part comprising a programming interface to the programming device, the programming device comprising a configuration extractor electrically connected to said second hearing device part via said programming interface and said connecting element and adapted to identify, from signals outputted respectively from said number of sensors and received by the first hearing device part via said connecting element, a current configuration of sensors in said second hearing device part.

19. A hearing system according to claim 18 wherein the programming device is configured to control the use of said sensors in said hearing device.

20. A hearing system according to claim 18 configured to identify each of said number of sensors individually to thereby identify the current configuration of sensors in said second hearing device part.

21. A hearing system according to claim 18, wherein each of the number of sensors is allocated a different one of the number of electric termination elements and associated electric conductors of the cable to transfer a respective electric sensor signal to the first hearing device part, and wherein an electric termination element and associated electric conductor of the cable, which is allocated to a specific one of the number of sensors, is supplied with a predefined signal, when said specific sensor is absent from said second hearing device part.

22. A hearing system according to claim 18, wherein at least one of the number of sensors has a digital output and is adapted to communicate an identifier of said sensor to the first hearing device part via its allocated conductor or a conductor dedicated to data, and wherein the configuration extractor is adapted to decode said identifier.

23. A hearing system according to claim 18, wherein at least one of the number of sensors has an analogue output, and wherein the configuration extractor is adapted to identify said sensor based on its intrinsic noise signal and/or on an output signal from the sensor reflecting its normal function.

24. A hearing system according to claim 18, wherein the number of sensors comprises a microphone, and wherein the hearing device is configured to play a test sound signal, and wherein the configuration extractor is adapted to detect the test sound signal in the feedback signal received by said microphone, and to thereby identify the sensor as a microphone.

25. A hearing system according to claim 18, wherein the configuration extractor is adapted to compare an electric sensor signal from a particular sensor among said number of sensors before and after being located at or in an ear of a user, and based thereon to identify the particular sensor.

26. A hearing system according to claim 18, wherein the programming device is configured to run a fitting software for the hearing device.

27. A hearing system according to claim 18, wherein the hearing device comprises a hearing aid.

* * * * *